(12) United States Patent
Chu et al.

(10) Patent No.: US 9,050,164 B2
(45) Date of Patent: Jun. 9, 2015

(54) SYSTEMS AND METHODS FOR DELIVERING A MEDICAL IMPLANT TO AN ANATOMICAL LOCATION IN A PATIENT

(75) Inventors: Michael S. H. Chu, Brookline, MA (US); Alfred P. Intoccia, Jr., Amherst, NH (US); Tim Moore, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 102 days.

(21) Appl. No.: 13/458,384

(22) Filed: Apr. 27, 2012

(65) Prior Publication Data

US 2012/0215059 A1   Aug. 23, 2012

Related U.S. Application Data

(63) Continuation of application No. 12/776,951, filed on May 10, 2010, now Pat. No. 8,167,786, which is a continuation of application No. 10/957,926, filed on Oct. 4, 2004, now Pat. No. 7,713,187.

(60) Provisional application No. 60/569,300, filed on May 6, 2004, provisional application No. 60/508,600, filed on Oct. 3, 2003.

(51) Int. Cl.
*A61F 2/04* (2013.01)
*A61F 2/00* (2006.01)
(Continued)

(52) U.S. Cl.
CPC .......... *A61F 2/0045* (2013.01); *A61B 17/06109* (2013.01); *A61B 2017/0046* (2013.01); *A61B 2017/00805* (2013.01); *A61B 2017/06009* (2013.01); *A61B 2017/06019* (2013.01); *A61B 2017/06042* (2013.01);
(Continued)

(58) Field of Classification Search
CPC .......... A61B 17/0401; A61B 17/0487; A61B 17/06109; A61B 17/30; A61B 19/24; A61F 2/0045
USPC .......... 600/29–32, 37; 128/897, 898
See application file for complete search history.

(56) References Cited

U.S. PATENT DOCUMENTS 2,008,251 A  *  7/1935  Hillebrand .................... 606/146
3,565,073 A      2/1971  Giesy
(Continued)

FOREIGN PATENT DOCUMENTS

EP       0677297 B1    10/1995
EP       1201189 A2     5/2002
(Continued)

OTHER PUBLICATIONS

Delorme, "La Bandelette Trans-Obturatrice: Un Procede Mini-Invasif Pour Traiter l'incontinence Urinaire D'effort De La Femme," Progress En Urologie, 11:1306-1313 (2001).
(Continued)

*Primary Examiner* — Samuel Gilbert

(57) ABSTRACT

Medical implant delivery devices and systems are disclosed. In general, an exemplary delivery device comprises a shaft and a handle. An exemplary system includes any number of the following: a delivery device, a sling assembly, guide members, and connectors that interconnect the above. Embodiments of all the above components and their combinations are disclosed. Methods of using the above system in trans-obturator approaches are disclosed.

21 Claims, 28 Drawing Sheets

(51) Int. Cl.
 *A61B 17/06* (2006.01)
 *A61B 17/00* (2006.01)
 *A61B 17/29* (2006.01)

(52) U.S. Cl.
 CPC ............. *A61B 2017/06076* (2013.01); *A61B 2017/0608* (2013.01); *A61B 2017/06085* (2013.01); *A61B 2017/2927* (2013.01)

(56) References Cited

U.S. PATENT DOCUMENTS

| | | | |
|---|---|---|---|
| 3,704,712 | A | 12/1972 | Giesy et al. |
| 4,798,193 | A | 1/1989 | Giesy et al. |
| 4,824,435 | A | 4/1989 | Giesy et al. |
| 4,872,451 | A | 10/1989 | Moore et al. |
| 4,946,468 | A | 8/1990 | Li |
| 5,002,550 | A | 3/1991 | Li |
| 5,064,435 | A | 11/1991 | Porter |
| 5,078,730 | A | 1/1992 | Li |
| 5,084,058 | A | 1/1992 | Li |
| 5,152,749 | A | 10/1992 | Giesy et al. |
| 5,207,679 | A | 5/1993 | Li |
| 5,334,185 | A | 8/1994 | Giesy et al. |
| 5,439,467 | A | 8/1995 | Benderev et al. |
| 5,505,735 | A | 4/1996 | Li |
| 5,645,589 | A | 7/1997 | Li |
| 5,683,418 | A | 11/1997 | Luscombe et al. |
| 5,690,649 | A | 11/1997 | Li |
| 5,702,215 | A | 12/1997 | Li |
| 5,749,884 | A | 5/1998 | Benderev et al. |
| 5,830,220 | A | 11/1998 | Wan et al. |
| 5,860,993 | A | 1/1999 | Thompson et al. |
| 5,899,909 | A | 5/1999 | Claren et al. |
| 5,954,057 | A | 9/1999 | Li |
| 6,042,534 | A | 3/2000 | Gellman et al. |
| 6,050,937 | A | 4/2000 | Benderev |
| 6,096,041 | A | 8/2000 | Gellman et al. |
| 6,099,547 | A | 8/2000 | Gellman et al. |
| 6,200,330 | B1 | 3/2001 | Benderev et al. |
| 6,264,676 | B1 | 7/2001 | Gellman et al. |
| 6,273,852 | B1 | 8/2001 | Lehe et al. |
| 6,423,080 | B1 | 7/2002 | Gellman et al. |
| 6,475,139 | B1 | 11/2002 | Miller |
| 6,478,727 | B2 | 11/2002 | Scetbon |
| 6,491,703 | B1 | 12/2002 | Ulmsten |
| 6,494,887 | B1 | 12/2002 | Kaladelfos |
| 6,530,943 | B1 | 3/2003 | Hoepffner et al. |
| 6,596,001 | B2 | 7/2003 | Stormby et al. |
| 6,605,097 | B1 | 8/2003 | Lehe et al. |
| 6,612,977 | B2 | 9/2003 | Staskin et al. |
| 6,638,209 | B2 | 10/2003 | Landgrebe |
| 6,638,210 | B2 | 10/2003 | Berger |
| 6,638,211 | B2 | 10/2003 | Suslian et al. |
| 6,641,525 | B2 | 11/2003 | Rocheleau et al. |
| 6,648,921 | B2 | 11/2003 | Anderson et al. |
| 6,652,450 | B2 | 11/2003 | Neisz et al. |
| 6,685,629 | B2 | 2/2004 | Therin |
| 6,691,711 | B2 | 2/2004 | Raz et al. |
| 6,802,807 | B2 | 10/2004 | Anderson et al. |
| 6,830,052 | B2 | 12/2004 | Carter et al. |
| 6,872,227 | B2 | 3/2005 | Sump et al. |
| 6,911,003 | B2 * | 6/2005 | Anderson et al. ............... 600/30 |
| 6,936,054 | B2 | 8/2005 | Chu |
| 7,070,556 | B2 | 7/2006 | Anderson et al. |
| 7,204,802 | B2 | 4/2007 | De Leval |
| 7,524,281 | B2 | 4/2009 | Chu et al. |
| 7,713,187 | B2 | 5/2010 | Chu et al. |
| 2001/0037119 | A1 | 11/2001 | Schmieding |
| 2001/0053916 | A1 | 12/2001 | Rioux |
| 2002/0072694 | A1 | 6/2002 | Snitkin et al. |
| 2002/0077526 | A1 | 6/2002 | Kammerer et al. |
| 2002/0091298 | A1 | 7/2002 | Landgrebe |
| 2002/0147382 | A1 | 10/2002 | Neisz et al. |
| 2002/0151909 | A1 | 10/2002 | Gellman et al. |
| 2002/0156489 | A1 | 10/2002 | Gellman et al. |
| 2002/0188169 | A1 | 12/2002 | Kammerer et al. |
| 2003/0009181 | A1 * | 1/2003 | Gellman et al. ............... 606/151 |
| 2003/0045892 | A1 | 3/2003 | Kaladelfos |
| 2003/0065246 | A1 | 4/2003 | Inman et al. |
| 2003/0149440 | A1 | 8/2003 | Kammerer et al. |
| 2003/0171644 | A1 | 9/2003 | Anderson et al. |
| 2003/0176762 | A1 | 9/2003 | Kammerer |
| 2003/0176875 | A1 | 9/2003 | Anderson et al. |
| 2003/0204191 | A1 | 10/2003 | Saterer et al. |
| 2003/0212305 | A1 | 11/2003 | Anderson et al. |
| 2004/0087970 | A1 | 5/2004 | Chu et al. |
| 2004/0097974 | A1 | 5/2004 | De Leval et al. |
| 2004/0106846 | A1 | 6/2004 | Gellman |
| 2004/0133217 | A1 | 7/2004 | Watschke |
| 2004/0144395 | A1 | 7/2004 | Evans et al. |
| 2004/0230206 | A1 | 11/2004 | Gellman et al. |
| 2005/0021086 | A1 | 1/2005 | De Leval et al. |

FOREIGN PATENT DOCUMENTS

| | | |
|---|---|---|
| WO | 97/16121 A1 | 5/1997 |
| WO | 98/34545 | 8/1998 |
| WO | 98/35632 | 8/1998 |
| WO | 01/78609 A2 | 10/2001 |
| WO | 01/93656 A2 | 12/2001 |
| WO | 02/19945 A2 | 3/2002 |
| WO | 03/007847 A1 | 1/2003 |
| WO | 03/101344 A1 | 12/2003 |
| WO | 2004/019786 A1 | 3/2004 |

OTHER PUBLICATIONS

Ulmsten, et al, "An Ambulatory Surgical Procedure Under Local Anesthesia for Treatment of Female Urinary Incontinence", The International Urogynecology Journal, 7:81-86 (1996).
Office Action for EP Application No. 14157436.8, mailed May 20, 2014, 7 pages.
EP Search Report for EP Application No. 14157436.8, mailed May 9, 2014, 3 pages.

* cited by examiner

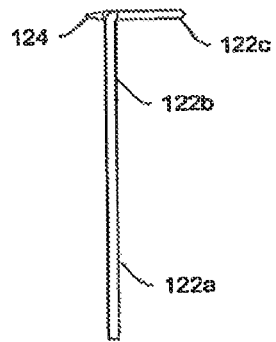
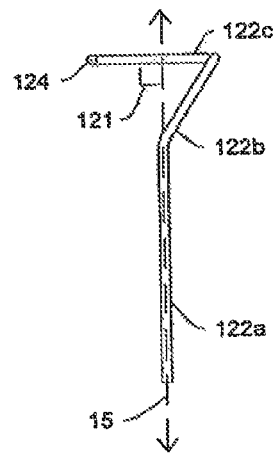
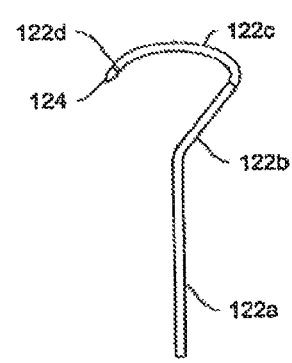
FIG. 11A
FIG. 11B          FIG. 11C          FIG. 11D

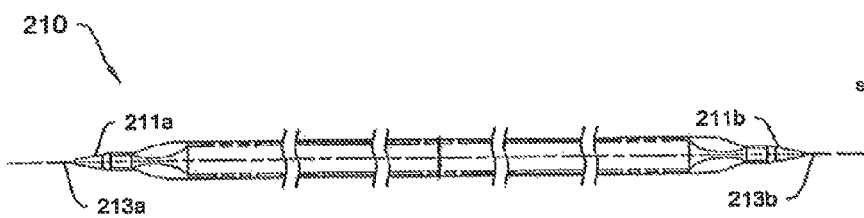
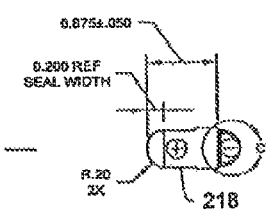
FIG. 20A　　　　　　　　FIG. 20D
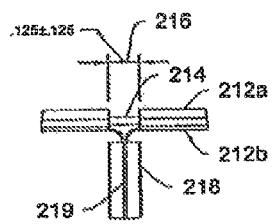
FIG. 20B
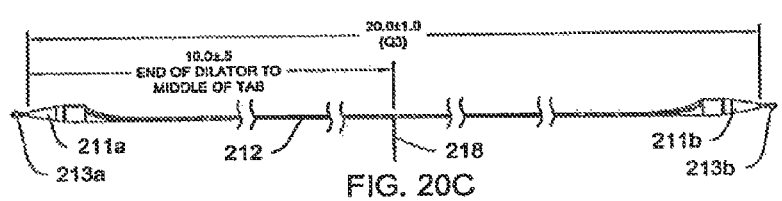
FIG. 20C

SYSTEMS AND METHODS FOR DELIVERING A MEDICAL IMPLANT TO AN ANATOMICAL LOCATION IN A PATIENT

CROSS REFERENCE TO RELATED APPLICATIONS

This application is a continuation of U.S. application Ser. No. 12/776,951, filed on May 10, 2010, which is a continuation of U.S. application Ser. No. 10/957,926, filed on Oct. 4, 2004, now U.S. Pat. No. 7,713,187, which claims the benefit of and priority to U.S. Provisional Patent Application Ser. No. 60/508,600 filed on Oct. 3, 2003 and U.S. Provisional Patent Application Ser. No. 60/569,300, filed on May 6, 2004, which are hereby incorporated by reference in their entirety.

FIELD OF THE INVENTION

The invention generally relates to systems and methods for delivering a medical implant to an anatomical location in a patient. More particularly, in various embodiments, the invention relates to systems and methods for employing a trans-obturator approach for delivering a medical implant to the periurethral tissue of a patient.

BACKGROUND OF THE INVENTION

Urinary incontinence ("UI") occurs in both men and women. Various types of incontinence are caused by different conditions and call for different treatments. For example, stress urinary incontinence ("SUP") is known to be caused by at least two conditions, intrinsic sphincter deficiency ("ISD") and hypermobility. One way to treat UI, both in men and women, is to place a surgical sling or suture in the periurethral tissue such as under the bladder neck or the urethra to provide a urethral platform. Placement of the sling limits mobility of the bladder neck or limits the endopelvis fascia drop while providing compression under event stress to improve urinary function. The sling may be affixed using a bone anchoring method. Alternatively, an operator can use an anchorless approach to stabilize the urethra with a sling by placing the sling in the periurethral tissue and relying on tissue compression and eventual tissue in-growth to secure the sling in position.

Various transvaginal and suprapubic approaches have been used for sling placement. However, one deficiency that such conventional procedures suffer from is that there is some risk of puncturing the patient's bladder.

Accordingly, devices, systems, and methods that reduce the risk of bladder injury are advantageous,

SUMMARY OF THE INVENTION

The invention addresses deficiencies of the prior art by, in one embodiment, providing delivery devices, systems, and methods for facilitating delivery of an implant to an anatomical site by way of the obturator foramen. In particular, the invention provides delivery devices, systems, and methods for placing an implant, e.g., a sling for treating UI (including SUI), by a trans-obturator approach. In one aspect, the invention provides a delivery device for delivering a supportive sling to the periurethral tissue of a patient via the obturator foramen of the patient.

In one embodiment, the delivery device includes a handle and a shaft extending from a distal end of the handle. The shaft may include one or more substantially straight sections and/or one or more curved sections. In some configurations, the shaft and the handle are substantially in the same plane. In other configurations, at least one section of the shaft and the handle are located in different planes. In some configurations, the shaft is located substantially in one plane. In other configurations, the shaft includes sections located in different planes. Preferably, the section(s) of the shaft that extend into the patient's body are located substantially in a single plane.

In certain embodiments, the delivery device may also include a transitional portion comprising one or more sections. The transitional portion interfaces between a gripping section of the handle and a tissue-penetrating section of the shaft. The transitional portion may be formed as part of the handle. Alternatively, the transitional portion may be formed as part of the shaft. The transitional portion may be formed from the same material as the shaft. Alternatively, the transitional portion may be formed from the same material as the handle. Additionally, the transitional portion may have a substantially constant diameter along its length. Alternatively, the transitional portion may have a varying diameter. In some configurations, the diameter of the transitional portion tapers as it extends axially in a distal direction. In other configurations, the diameter of the transitional portion is stepped to have sections of decreased diameter as it extends axially in a distal direction. The various sections of the shaft, the transitional portion and the handle may locate substantially in the same plane. Alternatively, the various sections of the shaft, the transitional portion and the handle may locate in different planes.

According to one preferred embodiment, the shaft includes an L-slot at its distal end. The L-slot may be particularly shaped to enable an association loop from a sling assembly to be hooked onto it during sling placement. In one configuration the L-slot is formed from first and second channels. The first channel is about 2 mm in length and about 1 mm in width and extends radially into the shaft. The second channel is about 5 mm in length and about 1 mm in width and extends distally along the length of the shaft from an inner terminal end of the first channel. In some alternative configurations, the second channel extends proximally, rather than distally, or in both directions from an inner terminal end of the first channel. In some configurations, the first channel of the L-slot extends into the shaft from a radially inner location along the surface of the shaft. However, in other embodiments, the first channel of the L-slot extends into the shaft from a radially outer surface of the shaft.

An important advantage of the L-slot configuration of the shaft is that an association loop, when hooked onto the L-slot, remains free to slide along the second channel. Another advantage is that, in one configuration, when slid to a proximal most position in the second channel, the association loop may be slid radially out of the first channel to unhook the association loop from the delivery devices. Alternatively, according to another preferred embodiment, during withdrawal of the delivery device, the distally extending orientation of the second channel causes the association loop to slide to a distal most position in the second channel. This tends to maintain the association loop hooked onto the second channel during delivery device withdrawal.

According to one aspect, the invention is directed to a system for delivering a supportive sling to the periurethral tissue of a patient, via a trans-obturator approach. In some embodiments, the system includes two delivery devices and a sling assembly. According to one such embodiment, the sling assembly includes a knitted mesh and a sleeve. Each end of the sleeve connects to a dilator. Each dilator, in one configuration, is a rigid polymer tube about 2 cm in length terminating in a conical tip. The dilators act to secure the association loops, to transition from the sling assembly to the association loops, and to expand tissue along a respective path during sling assembly placement. Embedded along the length of each dilator are two ends of a wire formed from twisted metal strands. The wire extends from the conical tip of each dilator to form an association loop. The association loop extending from each conical tip is about 15 mm in length. The association loop is deformable, but generally shape-retaining.

According to one embodiment, the knitted mesh is free floating within the sleeve. For one configuration of this embodiment, an opening, located at a midpoint of a top portion of the sleeve, exposes the entire width of the knitted mesh. Preferably, the knitted mesh is made of polypropylene, is about 1 cm in width and about 45 cm in length, and terminates at free ends. According to one configuration, the entire length of the knitted mesh, including both free ends, does not connect to the sleeve or anything else. This feature enables a medical operator to pull on the ends of the sleeve during sling assembly placement, for example, via the dilators, the association loops, and/or the delivery devices, without risk of stretching, curling, or otherwise deforming the knitted mesh.

According to another feature, a tabbed spacer is located at a midpoint of a bottom side of the sleeve, and encloses a looped portion of the bottom side of the sleeve. The tabbed spacer can be used during implantation as a visual aid to placement of the knitted mesh. The tabbed spacer also engages the looped portion of the bottom side of the sleeve and prohibits the sleeve from sliding off, or otherwise being removed from, the knitted mesh during sling assembly placement. Preferably, the tabbed spacer is cut to enable the sleeve to slide off the knitted mesh. This feature ensures that the sleeve cannot be removed simply by applying a pulling force, such as that applied to the sling assembly ends by a medical operator during sling assembly placement. After the sling assembly is positioned within the patient, a cut is made through the center of the tabbed spacer, and thus through the looped portion of the bottom side of the sleeve. The sleeve is then slid off of the knitted mesh, out of the body of the patient, and discarded, along with the dilators.

According to one method of use, the shaft of a delivery device is employed to create passages through body tissue, namely, from the inferior pubic ramus through the obturator foramen to the vagina. Three incisions are made in the body of the patient. A first incision is made just to the side of the edge of the ishiopubic ramus at the level of the clitoris. A second incision, corresponding to the first incision, is made on the contralateral side. A third incision is made in the anterior vaginal wall. The delivery device is held by the handle with one hand and is inserted through one ishiopubic incision in a downward motion, piercing the obturator muscle and obturator membrane. Then, the handle is turned to a position about 45 degrees to the vertical midline of the patient's body. A forefinger of the other hand is placed in the vaginal incision and on the distal end of the delivery device. The forefinger is used to guide the distal end around the ishiopubic ramus through the vaginal incision.

Next, the first association loop is slid over the distal end of the shaft of the delivery device and radially into the first channel of the L-slot. The association loop is then moved distally away from the delivery device within the second channel to hook one end of the sling assembly onto the delivery device. The delivery device is then withdrawn from the ishiopubic incision, drawing the end of the sling assembly through the passage created by the shaft. The orientation of the L-slot on the shaft with respect to the ishiopubic approach ensures that the association loop is tensioned toward the closed, distal end of the L-slot as the delivery device is withdrawn. Subsequent to withdrawal, the association loop is unhooked from the delivery device. This process is repeated with the same or a second delivery device and the second association loop on the contralateral side of the body. Optionally, a single cystoscopy may be performed with two delivery devices in place, prior to withdrawal of the delivery devices to verify integrity of the bladder. Cystoscopy may also be performed, as desired, after each placement of a delivery device on a side of the body. Alternatively, cystoscopy may be performed after withdrawal of both delivery devices.

According to another method of use, the shaft of a delivery device creates passages through body tissue from the vagina through the obturator foramen and through the inferior pubic ramus. Once again, three incisions are made in the body of the patient. A first incision is made just to the side of the edge of the ishiopubic ramus at the level of the clitoris. A second incision, corresponding to the first incision, is made on the contralateral side. A third incision is made in the anterior vaginal wall. In this procedure, the L-slot is positioned with the second channel extending proximally along the shaft, rather than distally, and the first association loop is hooked into the L-slot at the distal end of the shaft of the delivery device prior to inserting into the patient. The delivery device is inserted through the vaginal incision in a lateral motion passing behind the ishiopubic ramus, and piercing the obturator membrane and the obturator muscle and exiting the ishiopubic incision. The delivery device can be unhooked from first association loop and withdrawn from the body. This process is repeated with the same or a second delivery device and the second association loop on the contralateral side of the body. Optionally, a single cystoscopy may be performed with two delivery devices in place, prior to withdrawal of the delivery devices to verify integrity of the bladder. Cystoscopy may also be performed, as desired, after each placement of a delivery device on a side of the body. Alternatively, cystoscopy may be performed after withdrawal of both delivery devices.

Other movements may be employed, wherein the delivery device is first inserted into a vaginal incision, through the obturator membrane and the obturator muscle, and exiting from a ishiopubic.

The dilators may be used as handles to adjust the position of the sling assembly to achieve desired placement. Once desired placement of the sling assembly is achieved, the tabbed spacer, and thus the looped portion of the bottom side of the sleeve, may be cut. Then, by pulling upward on the dilators, the medical operator can slide the sleeve off the knitted mesh and remove it from the body. The delivery devices and the sleeve, including the dilators, can then be discarded.

In a variation of this approach, the delivery devices do not include any L-slots and the sling assembly includes a guide tube extending from each end of the sling assembly in place of the association loops. In such a configuration, the shaft of each respective delivery device can be inserted into a respective guide tube at the end of the guide tube closest to the sling assembly. According to one method, the vagina to ishiopubic methodology is employed, rather than the ishiopubic incision to vagina methodology, and subsequent to the distal end of a shaft exiting the ishiopubic incision, a medical operator grasps the end of the guide tube, for example, with forceps and withdraws the delivery device.

According to one aspect, the shaft of a delivery device includes a substantially straight section, a curved section and a transitional portion, all lying substantially in a single plane. The transitional portion includes a first and a second substantially straight sections and a curved section. The first substantially straight section of the transitional portion attaches to a distal end of the handle, extends distally along a first axis, and preferably has a substantially constant diameter. The curved section of the transitional portion extends from a distal end of the first straight section of the transitional portion, curves away from the first axis, and also preferably has a substantially constant diameter. The second substantially straight section of the transitional section extends from a distal end of the curved section of the transitional portion along a second axis, and preferably has an outside diameter that decreases from its proximal end to its distal end to provide increased structural stability to the shaft. The curved section of the shaft preferably has a substantially constant diameter, extends from the distal end of the transitional portion, curves back toward the first axis, and terminates at a distal end approximately at an intersection with the first axis. The substantially straight section of the shaft preferably has a substantially constant diameter, and extends from the distal end of the curved section of the shaft along a third axis, which crosses the first axis. The substantially straight section of the shaft terminates at a distal end to form a conical tip. The transitional portion may be formed from the same materials as the shaft, or alternatively, from the same material as the handle. Preferably, the shaft is formed of surgical grade stainless steel. In a preferred embodiment, only the curved section and the substantially straight section of the shaft penetrate into the body of a patient during sling placement.

In another aspect, the shaft includes a first straight section extending along an axis distally from the distal end of the handle and a first curved section, which initially curves away and then back across the axis of the first straight section. The shaft also includes a second curved section, in one configuration, having a radius larger than the radius of the first curved section. Like the first curved section, the second curved section initially curves away from and than back toward the axis of the first straight section. A second straight section extends from a distal end of the second curved section. In some configurations, the second straight section may or may not ultimately cross the axis of the first straight section. As in the case of previously discussed embodiments, the shaft may terminate in a conical tip, and may include an L-slot at its distal end for associating with a sling assembly or other medical implant. One advantage of having the tip extend across the axis of the first straight section is that it provides increased ease with which the medical operator can puncture through the obturator membrane in a trans-obturator approach, and reduces the likelihood of the handle getting in the way. Additionally, the apex of the curve having the smaller radius can act as a fulcrum to enable the physician to have more control when inserting the shaft.

In some multiple curve embodiments, the first curved section extends first distally along a longitudinal axis of the handle, then reverses direction to extend back proximal of the distal end of the handle. The second curved section then curves the shaft back in a distal direction.

In another aspect of the invention, a first section of the handle of the delivery device extends along a first axis substantially in a first plane. A second section of the handle extends distally from, but along a second axis at an angle to, the first axis, which is substantially in the same plane as the first section of the handle. In one configuration, a shaft having a curved section first extends out of the first plane of the first and second handle sections, then extends back toward the first plane. In some configurations, the distal tip of the shaft extends back through the first plane. In other configurations, the distal tip extends up to or short of the first plane. In a related embodiment, the delivery device also includes a transitional portion having one or more sections located substantially in the first plane and extending between the handle and the curved section of the shaft for providing added structural support to the curved section of the shaft and/or for facilitating interconnection between the curved section of the shaft and the distal end of the handle. In one configuration, the transitional portion includes the second section of the handle and a substantially straight section of the shaft. In a preferred embodiment, the one or more transitional sections do not penetrate into the body tissue of a patient during sling placement.

According to one feature, the shaft rotates about an axis that is substantially orthogonal to the first plane. According to other features, the axis need not be substantially orthogonal to the first plane. In some configurations, the axis is in a second plane parallel to the first plane. According to another embodiment, the at least one of the first and second sections of the handle tapers to be narrower as the handle extends distally toward the shaft.

In a further aspect of the invention, a first section of the shaft of the delivery device extends out of the handle along a first axis substantially in a first plane. A section of the shaft extends distally from, but at an angle to the first section of the shaft, and substantially in the same plane as the first section of the shaft. A third shaft section including a curved portion first extends out of the first plane of the first and second shaft sections, then extends back toward the first plane. In some configurations, the distal tip of the shaft extends back through the first plane.

In other configurations, the distal tip extends up to or short of the first plane. According to one embodiment, the third shaft section is in a plane that is substantially orthogonal to the axis of the first shaft section. However, in other embodiments, the plane is at a non-orthogonal angle to the axis of the first shaft section.

In various aspects of the invention, some sections of the shaft are moveable relative to other sections of the shaft. By way of example, in some embodiments a portion of the shaft can be manipulated or rotatable about an axis of the handle. The rotation can be used, for example, to adjust for a patients anatomy and/or to improve operator ergonomics. According to one configuration, the rotation encompasses up to about 360 degrees about an axis defined by the connection point between the shaft and the handle. By rotating the curved shaft, for example, up to about 180 degrees (e.g., up to, for example, 90 degrees about an axis, and from either side of the plane of the handle), the delivery device can be adapted for use on a lateral side and on a contralateral side of the patient.

According to other embodiments, a portion of the shaft can be tilted, for example up to about 90 degrees relative to the axis of the handle. In one construction, the delivery devices include discrete locking locations, for example, at about 0, 30, 45, 60 and/or 90 degrees relative to the axis of the handle. In other embodiments, a portion of the shaft extends distally out of the handle along an axis, and another portion of the shaft can be rotated about and/or tilted relative to the axis of the portion extending out of the handle. Preferably, after rotation and/or tilting to a desired position, the shaft may be secured at such a position relative to the handle. Any suitable mechanism may be employed for achieving such rotation, tilting, and/or locking.

The handle of a delivery device may be of various configurations. In preferred embodiments, the handle is of an ergonomic design and construction that reduces operator fatigue and discomfort, provides needed leverage and gripping surface for the user, orients the user as to the direction of the shaft, and/or provides fingertip or palm control over the shaft.

The handle may, for example, be cylindrical. Cross sections of the handle may have variable diameters, for example, at least one portion of the handle may have a cross section that is smaller than the adjacent portions of the handle to provide grooves for an operator to hold the handle. Alternatively, the cross section of a handle has a decreasing area from the proximal end to the distal end of the handle. The handle may have a substantially hexagonal cross section. Alternatively, the handle may be substantially T-shaped, D-shaped or kidney-shaped. Alternatively, the handle may be a ratchet type.

Additional features and advantages of the invention will be apparent from the following description of preferred embodiments and from the claims.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

FIGS. 11A-11D depict a delivery device having a shaft with two substantially straight sections located in a first plane and angled relative to each other, and a curved section located in a second plane at substantially a right angle to the first plane according to an illustrative embodiment of the invention.

FIGS. 20A-20D depict various views of an exemplary sling assembly of the type that may be employed in an illustrative embodiment of the invention.

ILLUSTRATIVE DESCRIPTION

Figure 1:
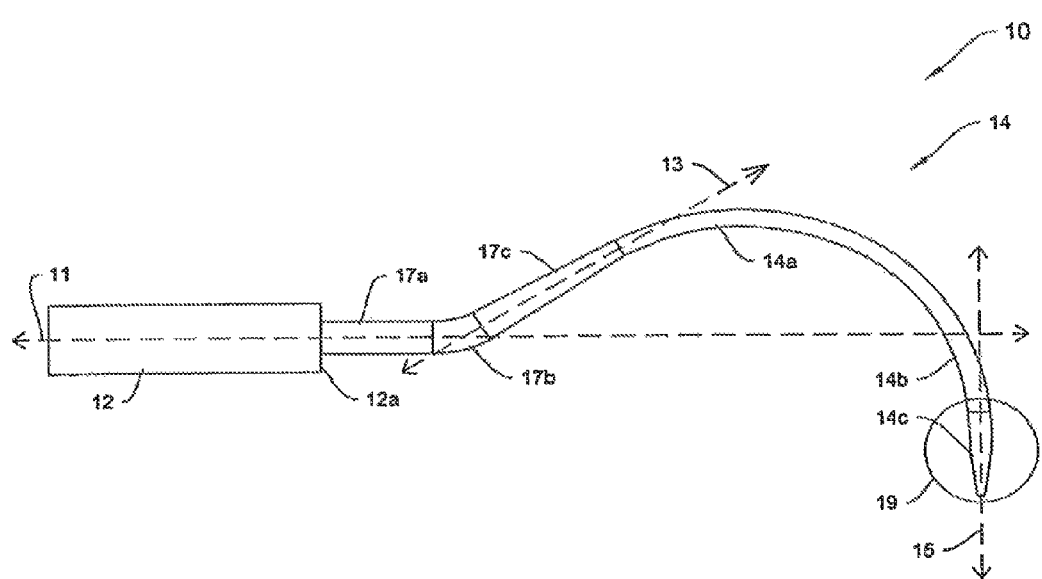
FIG. 1 is a side view of a delivery device according to an illustrative embodiment of the invention.

As described in summary above, the invention, in one illustrative embodiment, relates to systems and methods for delivering and placing a medical implant at an anatomical site in the body of a mammal. In particular, in various illustrative examples, the invention provides delivery devices, systems, and methods for placing an implant, e.g., a sling for treating UI (including SUI), by a trans-obturator approach. In one aspect, the implant includes a supportive sling and is delivered to the periurethral tissue of a patient via the obturator foramen. In one embodiment, the delivery device includes a handle and a shaft extending from a distal end of the handle. The patient may be either a female patient or a male patient.

Without limitation, examples of slings, sling assemblies, delivery devices and implantation approaches that may be employed with respect to some features of illustrative embodiments of the invention are disclosed in U.S. Pat. No.

6,666,817, entitled "Expandable surgical implants and methods of using them," U.S. Pat. No. 6,669,706, entitled "Thin soft tissue surgical support mesh," U.S. Pat. No. 6,375,662, entitled "Thin soft tissue surgical support mesh," U.S. Pat. No. 6,042,592, entitled "Thin soft tissue surgical support mesh," U.S. patent application Ser. No. 10/015,114, entitled "Devices for minimally invasive pelvic surgery," U.S. patent application Ser. No. 10/774,826, entitled "Devices for minimally invasive pelvic surgery," U.S. patent application Ser. No. 10/093,398, entitled "System for implanting an implant and method thereof," U.S. patent application Ser. No. 10/093,498, entitled "System for implanting an implant and method thereof," U.S. patent application Ser. No. 10/093,371, entitled "System for implanting an implant and method thereof," U.S. patent application Ser. No. 10/093,424, entitled "System for implanting an implant and method thereof," U.S. patent application Ser. No. 10/093,450, entitled "System for implanting an implant and method thereof," U.S. patent application Ser. No. 10/094,352, entitled "System for implanting an implant and method thereof," U.S. patent application Ser. No. 10/631,364, entitled "Bioabsorbable casing for surgical sling assembly," U.S. patent application Ser. No. 10/641,376, entitled "Spacer for sling delivery system," U.S. patent application Ser. No. 10/641,487, entitled "Systems, methods and devices relating to delivery of medical implants," U.S. patent application Ser. No. 10/642,395, entitled "Systems, methods and devices relating to delivery of medical implants," U.S. patent application Ser. No. 10/642,397, entitled "Systems, methods and devices relating to delivery of medical implants," U.S. patent application Ser. No. 10/832,653, entitled "Systems and methods for sling delivery and placement," the entire contents of all of which are incorporated herein by reference.

The invention addresses deficiencies of the prior art by, in various illustrative embodiments, providing delivery devices, systems, and methods for placing an implant, e.g., sling for treating UI (including SUI), by a trans-obturator approach. As described below in further detail, the illustrative delivery devices include a handle and a shaft extending from a distal end of the handle. The shaft may include one or more substantially straight sections and/or one or more curved sections. In some configurations, the shaft and the handle are substantially in the same plane. In other configurations, at least one section of the shaft and the handle are located in different planes. In some configurations, the shaft is located substantially in one plane. In other configurations, the shaft includes sections located in different planes. Preferably, the section(s) of the shaft that extend into the patient's body are located substantially in a single plane. The shaft may be, for example, any suitable needle, cannula, tubular member, tunneler, dilator, or the like. In a similar fashion, the handle may include sections located in different planes.

In certain embodiments, the delivery device may also include a transitional portion comprising one or more sections. The transitional portion interfaces between a gripping section of the handle and a tissue-penetrating section of the shaft. The transitional portion may be formed as part of the handle. Alternatively, the transitional portion may be formed as part of the shaft. The transitional portion may be formed from the same material as the shaft. Alternatively, the transitional portion may be formed from the same material as the handle. Additionally, the transitional portion may have a substantially constant diameter along its length. Alternatively, the transitional portion may have a varying diameter. In some configurations, the diameter of the transitional portion tapers as it extends axially in a distal direction. In other configurations, the diameter of the transitional portion is stepped to have sections of decreased diameter as it extends axially in a distal direction. The various sections of the shaft, the transitional portion and the handle may locate substantially in the same plane. Alternatively, the various sections of the shaft, the transitional portion and the handle may locate in different planes.

Preferably, the shaft is formed from a metal or a polymeric material. Examples of suitable metals include, but are not limited to, stainless steel, titanium, and alloys such as nitinol. Suitable polymers, which can be used as a coating on a metal to form the shaft, include but are not limited to, plastics such as polytetrafluoroethylene (PTFE). In some configurations, the shaft is rigid. However, in other configurations, the shaft has some flexibility, and can be described as semi-rigid. The shaft may have a conical tip at the distal end. The conical tip may configured for percutaneous punctuation and/or advancement through tissue. However, the tip may be blunt or sharp. A blunt tip provides some resistance to unintended penetration through tissue or organ, such as the bladder.

The shaft may be solid or hollow. If the shaft is at least partly hollow, it may include a lumen (not shown) that has one or more openings on the shaft, for example, at the distal tip or along the side of the shaft. The cross-section of the shaft may have a constant shape and size, or its shape and/or size may vary along its length. The cross-section of the shaft may assume any suitable shape, for example, circular, semi-circular, oval, triangular, or rectangular. In other embodiments, the distal end may include an enlarged, flared portion to dilate tissue beyond the nominal diameter of the shaft.

In one illustrative embodiment, the surface of the shaft is smooth and may be coated with one or more drugs such as anesthetic, anti-inflammatory, coagulating, anticoagulating, antibiotic, or antimicrobial agents. The drug may be delivered to the patient's tissue while the shaft is in contact with the tissue. The surface of the shaft may be coated with a light-absorbing coating to reduce glare, for example, under a cystoscope. The coating may be a polymer, such as Teflon, or other suitable material, and may be colored to aid in detection. The surface of the shaft may be painted so that one can easily tell it apart from surrounding tissue and fluid under a cystoscope to make it easier to detect under the cystoscope. In other illustrative embodiments, the shaft is textured, for example, by stippling, to provide increased traction relative to a gloved hand of a medical operator. In another illustrative embodiment, the shaft is fitted with a colored sheath, such as a blue plastic sheath or a guide tube.

FIG. 1 depicts a side view of a delivery device 10 according to an illustrative embodiment of the invention. The delivery device 10 includes a handle 12, a shaft 14, and a transitional portion extending distally between a distal end 12a of the handle 12 and a proximal end of the shaft 14. The transitional portion 17 includes a first straight section 17a, a curved section 17b and a second straight section 17c all lying substantially in as single plane, and may be formed as either part of the shaft 14 or as part of the handle 12. The shaft 14 includes a curved section 14a, a straight section 14b and a conical tip 14c, all lying substantially in the same plane as the transitional portion 17. In the illustrative embodiment, the first straight section 17a of the transitional portion 17 attaches to the distal end 12a of the handle 12, extends distally along a first axis 11, and preferably has a substantially constant diameter. The curved section 17b of the transitional portion 17 extends from a distal end of the first straight section 17a, curves away from the first axis 11, and also preferably has a substantially constant diameter. The second straight section 17c extends from a distal end of the curved section 17b along a second axis 13, and preferably has a diameter that decreases from its proximal end to its distal end to provide increased structural stability to the shaft 14. The curved section 14a, preferably, has a substantially constant diameter, smaller than the diameter of the curved section 17b of the transitional portion 17, and extends from the distal end of the second straight section 17c of the transitional portion 17, curves back toward the first axis 11, and terminates at a distal end approximately at an intersection with the first axis 11. The straight section 14b, preferably, has a substantially constant diameter and extends from the distal end of the curved section 14a along a third axis 15, which crosses the first axis 11. A conical tip 14c extends distally from the straight section 14b. As discussed below in further detail with regard to FIG. 22, the distal end 19 of the delivery device 10 may include a structure for associating the delivery device 10 with a sling assembly. Preferably, the shaft 14 is formed of surgical grade stainless steel.

Figure 2:
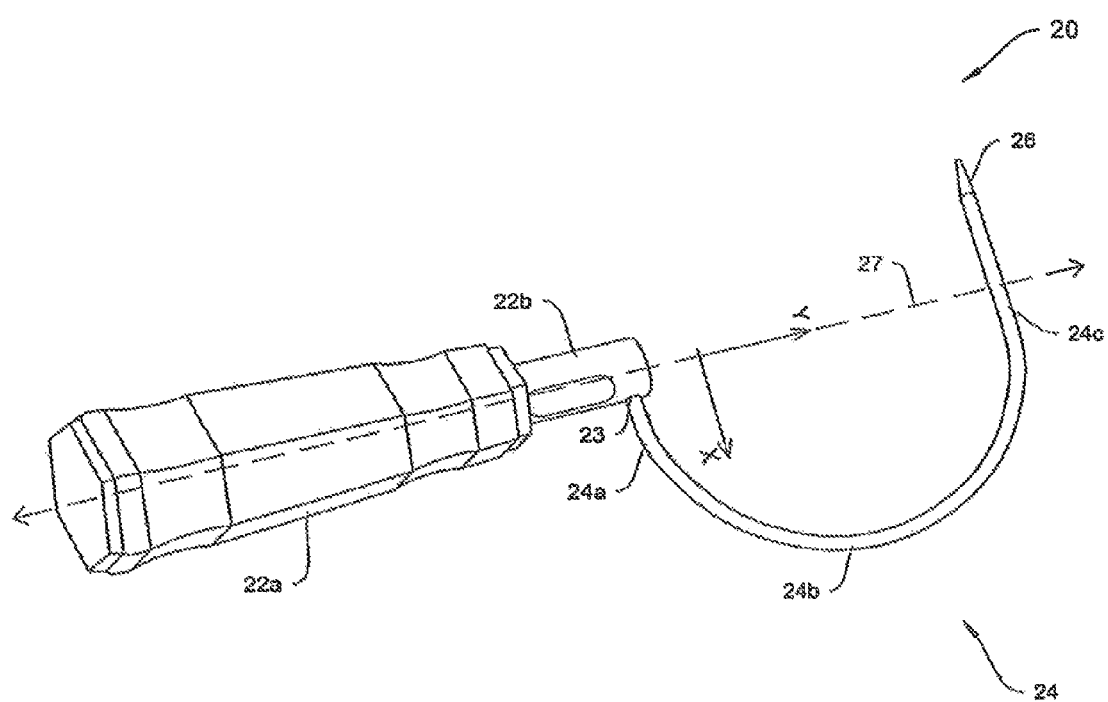
FIG. 2 is a perspective side view of a delivery device having a shaft with a curved section according to another illustrative embodiment of the invention.

FIG. 2 depicts a perspective side view of a delivery device 20 according to another illustrative embodiment of the invention. The delivery device 20 includes a shaft 24 and a handle 22. The handle 22 includes a base portion 22a and a handle extension/transitional portion 22b. The shaft includes a first straight section 24a extending axially from a connection location 23 in the handle extension/transitional portion 22b, a curved section 24b extending from a distal end of the first straight section 24a, a second straight section 24c extending from a distal end of the curved section 24b, and a conical tip 26 extending from a distal end of the second straight section 24c. The shaft 24 has a substantially C shape. As depicted, the shaft 24, the handle extension/transitional portion 22b, and the handle base 22a are all substantially coplanar. According to the illustrative embodiment of FIG. 2, the distal end of the shaft 24 crosses the axis 27 of the handle 22. More particularly, the curved section 24b falls short of the axis 27, but the second straight section 24c crosses it. In other embodiments the distal most ends of the conical tip 26, the second straight section 24c or the curved section 24b may extend past, fall short of or extend up to the axis 27.

Figure 3:
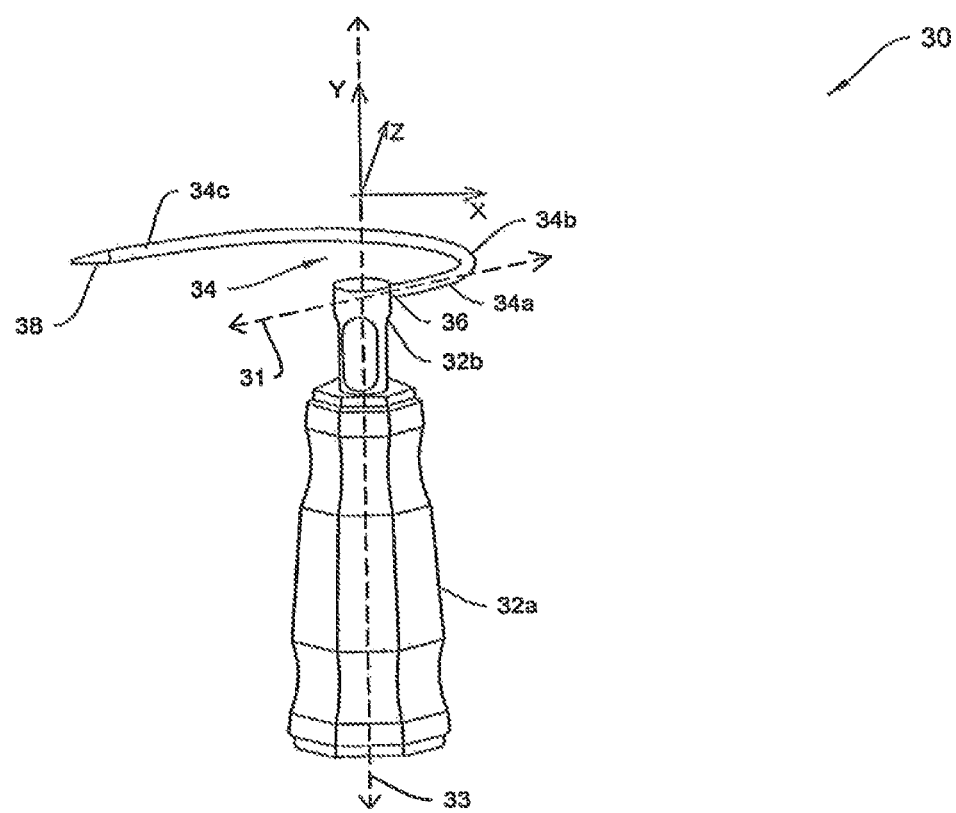
FIG. 3 depicts a delivery device having a shaft with a curved portion tilted at about ninety degrees relative to an axis of its handle according to another illustrative embodiment of the invention.

FIG. 3 depicts a delivery device 30 according to another illustrative embodiment of the invention. The delivery device 30 includes a shaft 34 and a handle 32. The handle 32 includes a base portion 32a and a handle extension/transitional portion 32b. The shaft 34 extends from a connection location 36 in the handle extension/transitional portion 32b, is shaped in a similar fashion to the Shaft 24 of FIG. 2 and includes a first straight section 34a, a curved section 34b, a second straight section 34c and a conical tip 38. The shaft 34 is rotated approximately 90 degrees about the axis 31 of the first straight section 34 to tilt the curved section 34b of shaft 34 about 90 degrees relative to the axis 33 of the handle 32.

Figure 4:
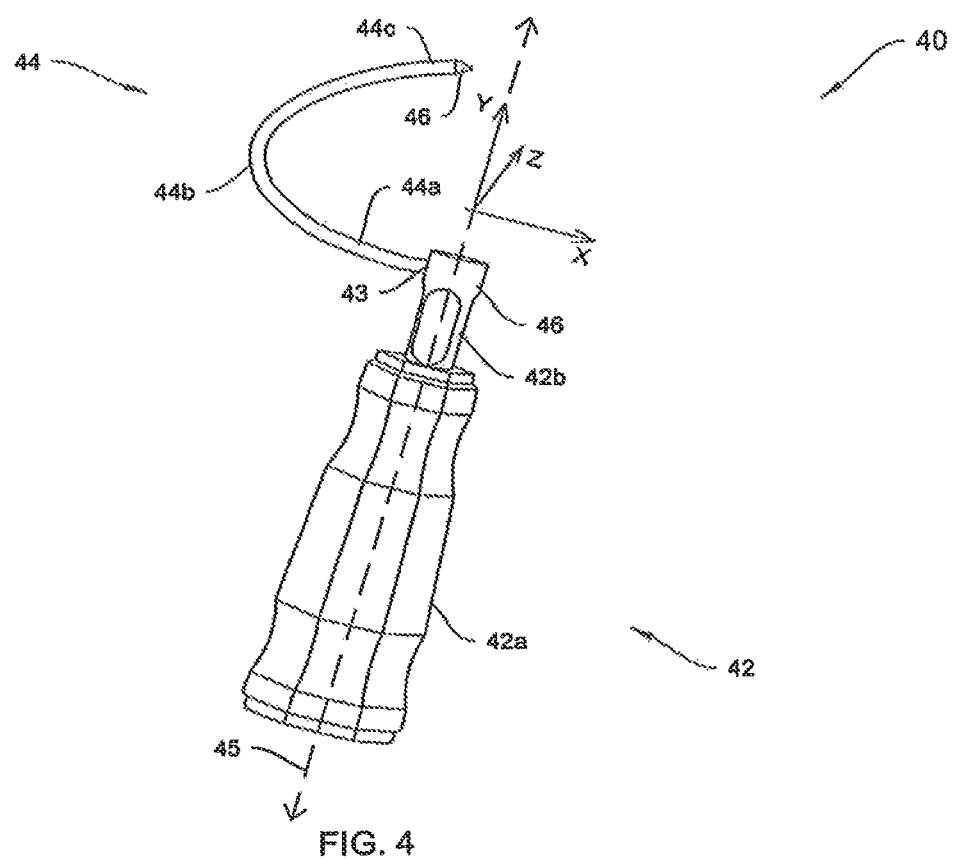
FIG. 4 depicts a delivery device having a shaft with a curved portion that extends through more than one plane according to another illustrative embodiment of the invention.

FIG. 4 depicts a delivery device 40 having a shaft 44 and a handle 42. As in the case of the illustrative embodiments of FIGS. 2 and 3, the handle 42 includes a base portion 42a and a handle extension/transitional portion 42b. The shaft 44 extends radially out of the connection location 43 in the handle extension/transitional portion 42b. Unlike the illustrative embodiments of FIGS. 2 and 3, the curved section 44b extends distally around the axis 45 of the handle 42 to form a portion of a spiral.

Figure 5:
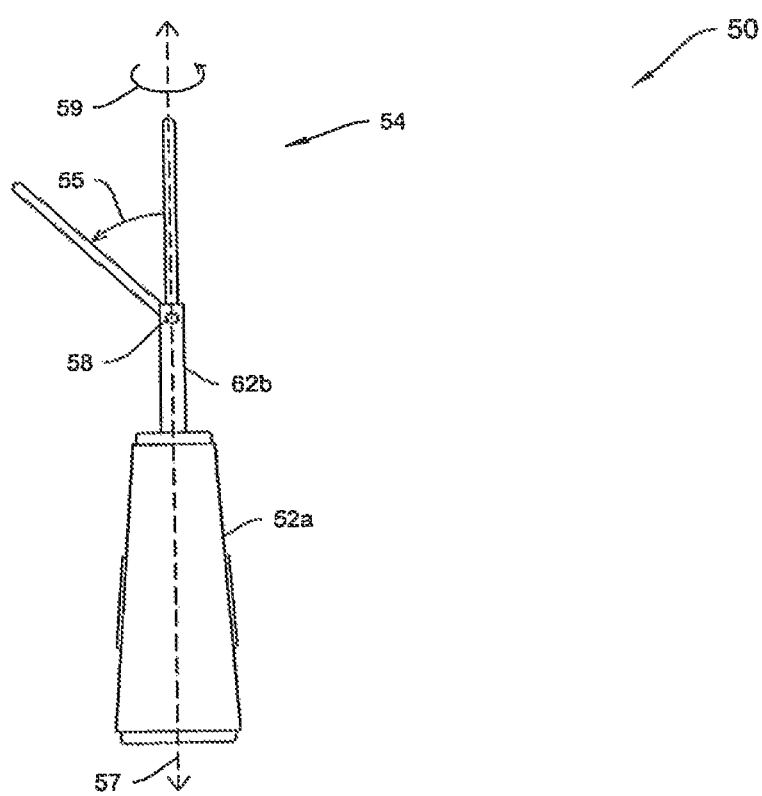
FIG. 5 is a side view of a delivery device having a shaft with a section that can be adjustably tilted relative to an axis of a handle according to an illustrative embodiment of the invention.

FIG. 5 is a side view of a delivery device 40 having a shaft 54 and a handle 52. The handle 52 has a base portion 52a and a handle extension 52b. The shaft 54 can be rotated by a medical operator in a controlled fashion through an angle 55 about a pivot 58 located at a distal end of the handle extension/transitional portion 52b to tilt the shaft 54 relative to an axis 57 of the handle 52. The shaft 54 is similarly shaped to the shaft 44 of FIG. 4. However, any suitably shaped shaft may be employed. Additionally, the pivot 58 is depicted as being located on the handle extension/transitional portion 52b, it may alternatively be located along the shaft 54, enabling a portion of the shaft 54 to be pivoted relative to another, for example, stationary portion of the shaft 54. According to the illustrative embodiment, the shaft may be pivoted through an angle of at least about 30, 60, 90, 120, 180, or up to about 360 degrees, or any degree of angle in between, limited in pivot only by contact with the handle on either side of the axis of the handle. Also, rather than being pivotable about the pivot 58, as indicated by the arrow 59, the shaft 54 or a portion of the shaft 54 may also or alternatively rotate radially about the axis 57. According to the illustrated embodiment, the shaft 43 may be rotated in either a clockwise or counter clockwise direction and through an angle of at least about 30, 60, 90, 120, 150, 180, 210, 240, 270, 300, 330, or 360 degrees. Shaft pivoting and/or rotation may be continuous in nature, for example, using a set screw to lock the shaft in place. Alternatively, it may be discrete in nature, for example, with gears, cogs, engaging surfaces or the like defining allowable shaft positions. A discrete configuration, for example, may have a spring loaded user-actuatable component to enable a medical operator to adjust the shaft position a desired.

Figure 6A:
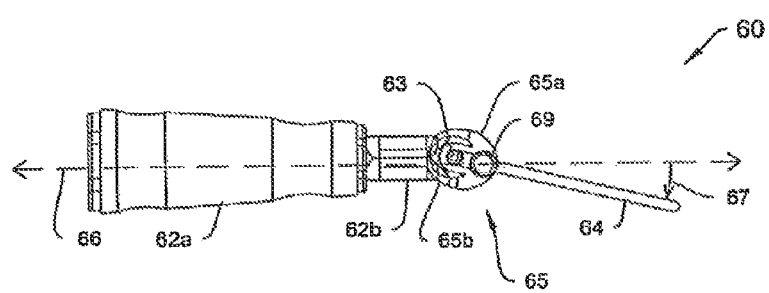
FIGS. 6A-6C depict an exemplary mechanical configuration for providing the adjustable tilting features of the illustrative delivery device of FIG. 5.
Figure 6B:
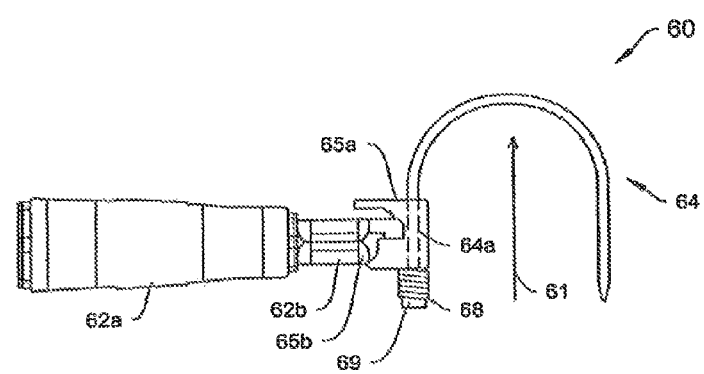
Figure 6C:
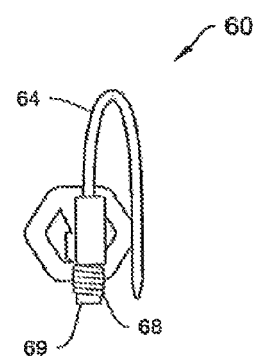

FIGS. 6A-6C depict an exemplary delivery device 60 including a mechanical configuration for providing the adjustable pivoting features of the illustrative delivery device 50 of FIG. 5. The delivery device 60 includes a shaft 64 and a handle 62. The handle 62 includes a base portion 62a and a handle extension/transitional portion 62b. The delivery device 60 also includes a pivot control mechanism 65. The pivot control mechanism 65 includes a housing 65a and features 65b on the handle extension/transitional portion 62b. As shown in FIG. 6B, a straight section 64a of the shaft 64 extends radially through the housing 65a. In operation, the housing 65a rotates about a pivot 63. A spring 68 loaded set screw 69 provides a mechanism for locking the shaft 64 in place. In alternative embodiments, the set screw 69 is calibrated so that the spring 68 is not fully compressed, and a medical operator can pull on the shaft 64 in the direction indicated by the arrow 61 to disengage the housing 65a from the features 65b and enable shaft pivoting. According to this embodiment, to lock the shaft 64 in place, the medical operator ceases pulling the shaft 64 in the direction indicated by the arrow 61, enabling the housing 65a and the features 65b to re-engage. Optionally, the set screw 69 can then be tightened to fully compress the spring 68 to ensure that the housing 65a is locked in place relative to the features 65b.

Figure 7:
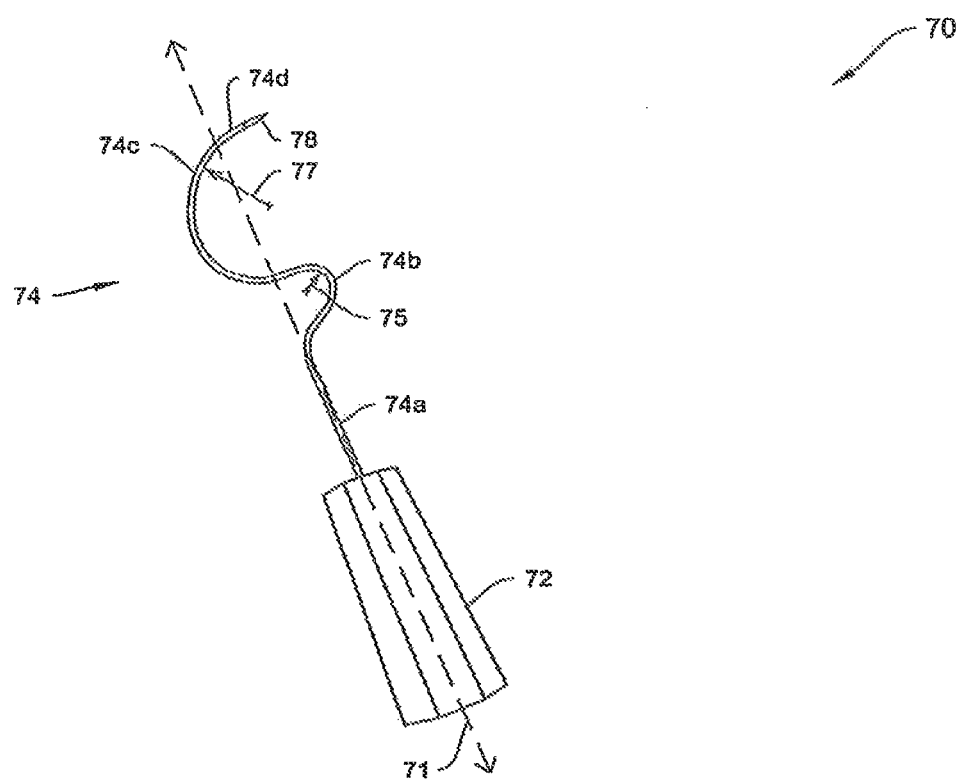
FIG. 7 is a perspective side view of a delivery device including two oppositely curving shaft sections according to an illustrative embodiment of the invention.

As mentioned above, in some illustrative embodiments, a shaft of the invention includes multiple curved sections. FIG. 7 depicts a delivery device 70 according to one such illustrative embodiment. The delivery device 70 includes a handle 72 and a shaft 74 extending distally from a distal end of the handle 72. According to this illustrative embodiment, the shaft includes a first straight section 74a extending distally from the distal end of the handle 72 along a longitudinal axis 74 of the handle 72. The shaft 74 also includes a first curved section 74b, which initially curves away and then back across the axis 71. A second curved section 74c, in one configuration, having a radius 77 larger than the radius 75 of the first curved section 74b, extends from a distal end of the first curved section 74b and initially curves away from and than back toward the axis 71. In the illustrative embodiment, a second straight section 74d extends from a distal end of the second curved section 74c. In various illustrative embodiments, the second straight section 74d may or may not ultimately cross the axis 71. According to one illustrative embodiment the tip 78 of the shaft 74 extends, for example, about 0.3 inches, about 0.3-1.0 inches, or about 0.54-0.75 inches past the axis 71. As in the case of previously discussed embodiments, the shaft 74 may terminate in a conical tip 78 and may include an L-slot at its distal end for associating with a sling assembly or other medical implant. One advantage of having the tip 78 closer to the patient is increased ease with which the shaft 74 can puncture through the obturator membrane in a trans-obturator approach. Another advantage is that it reduces the likelihood of the handle getting in the way. Moreover, the apex of the small radius 75 can act as a fulcrum, which enables a medical operator to have more control when inserting the shaft.

Figure 8:
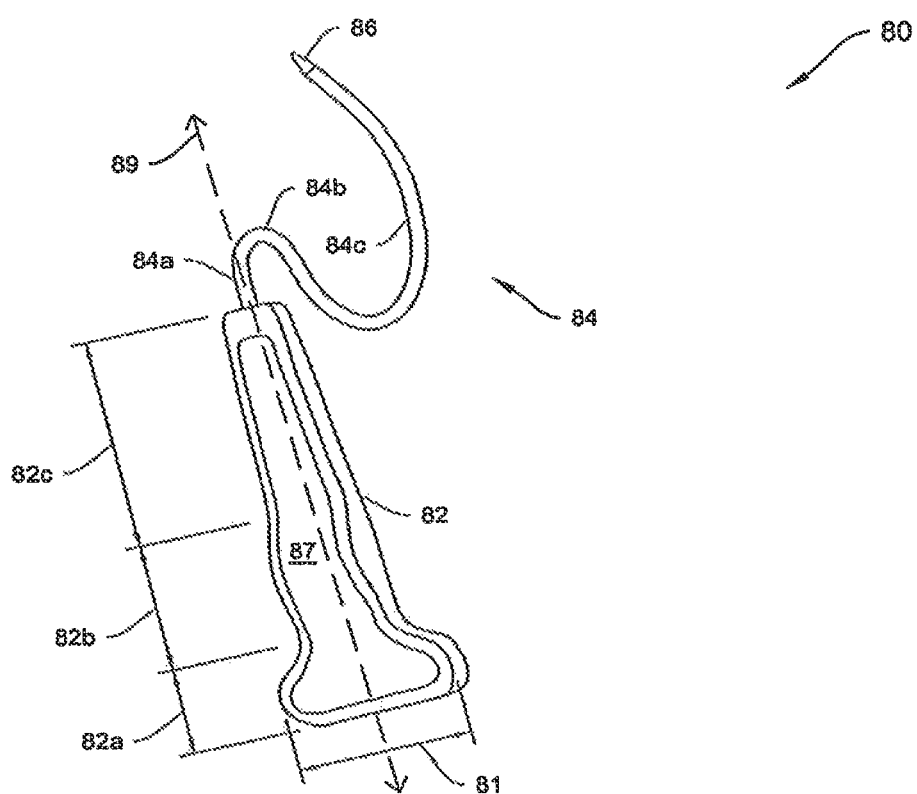
FIG. 8 is a perspective side view of a delivery device having a shaft with a section that curves proximally back toward its handle according to an illustrative embodiment of the invention.

FIG. 8 is a perspective side view of a delivery device 80 having a handle 82 and shaft 84 extending distally from a distal end of the handle 82. The handle 82 is ergonomically shaped, having a T-like configuration. The handle 82 has a width 81 that tapers to reduce the width 81 as the handle 82 extends from a proximal end to a distal end. The proximal end of the handle 82 includes a T-like feature 82a. The handle also includes a section 82b that is raised relative to the other handle sections 82a and 82c. The handle 82 also includes a textured portion 87 that further facilitates gripping of the delivery device 80. The shaft 84 includes a first straight section 84a that extends distally from a distal end of the handle 80 along a longitudinal axis 89 of the handle 80. A first curved section 84b first curves distally along the axis 89 then curves proximally back toward the handle 82, and a second curved section 84c then curves the shaft 84 back in a distal direction. The shaft 84, illustratively, terminates in a conical tip 86. The first 84b and second 84c curved shaft sections may or may not be substantially co-planar with each other and/or with the handle 82.

Figure 9A:
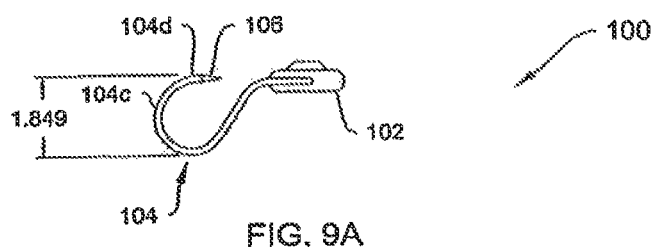
FIGS. 9A-9C depict various views of a delivery device having a shaft with coplanar straight sections and a partially spiralled section according to another illustrative embodiment of the invention.
Figure 9B:
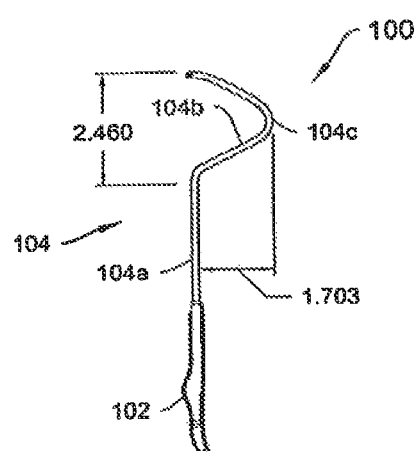
Figure 9C:
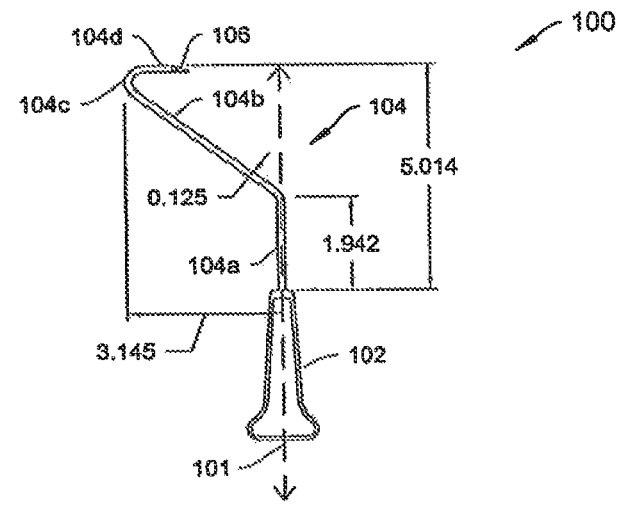

FIGS. 9A-9C depict various views of a delivery device 100 having a shaft 104 and a handle 102. The handle 102 is shaped similarly to the handle 82 of FIG. 8. The shaft 104 includes a first straight section 104a extending distally from the distal end of the handle 102 along a longitudinal axis 101 of the handle 102. The first straight section 104a of the shaft 104 is substantially coplanar in a first plane with the handle 102. A second straight section 104b of the shaft 104 extends distally from, but at an angle to the first straight section 104a. In the illustrative embodiment, the second straight section 104b is also substantially coplanar with the handle 102. A first curved section 104c of the shaft 104 extends from a distal end of the second straight section 104b and curves that shaft back toward the axis 101. A third straight section 104d of the shaft 104 extends from a distal end of the first curved section 104c. The first curved section 104c and the third straight section 104d are substantially coplanar with each other in a second plane. According to this illustrative embodiment, the first plane of the handle 102 and the second plane of the curved section 104c are angled relative to each other and are not the same plane. The shaft section of the delivery device 100 may be of constant cross sectional diameter or may have differing cross sectional diameters. Additionally, the shaft sections my have tapered cross sectional diameters to make for smooth surface transitions from one shaft section to the next. As depicted, the illustrative delivery device 100 terminates in a conical tip 106. However, this need not be the case, as any suitable tip may be employed. It should be noted that dimensions shown in FIGS. 9A-9B are all given in centimeters, are illustrative in nature, and are not intended to be limiting with regard to possible dimensions.

Figure 10A:
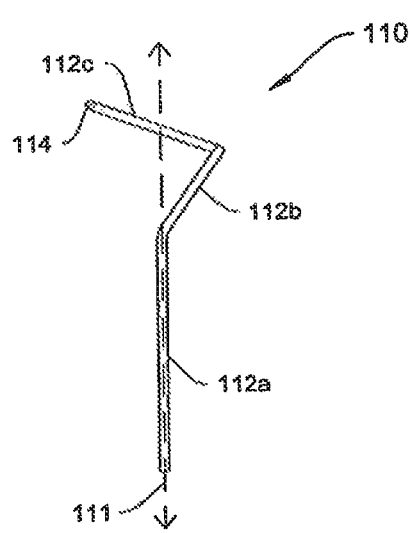
FIGS. 10A-10C depict a delivery device having a shaft with two substantially straight sections located in a first plane and angled relative to each other, and a curved section located in a second plane according to an illustrative embodiment of the invention.
Figure 10B:
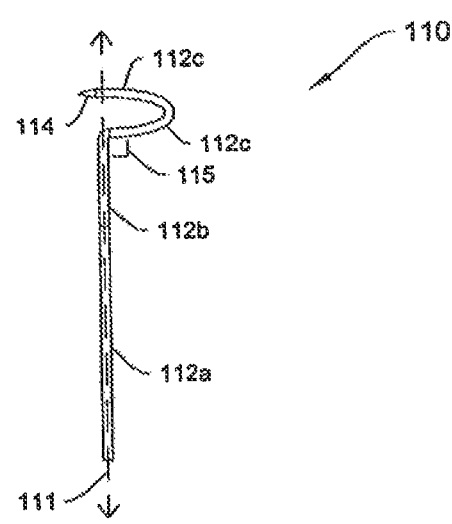
Figure 10C:
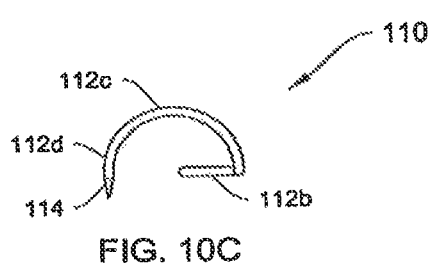

FIGS. 10A-10C depict various views of a delivery device 110 having a shaft 112. The shaft 112 is configured similarly to the shaft 104 of FIG. 9. More particularly, the shaft 112 includes a first straight section 112a extending distally along a longitudinal axis 111. A second straight section 112b of the shaft 112 extends distally from, but at an angle to the first straight section 112a. In the illustrative embodiment, the second straight section 112b is substantially coplanar in a first plane with the first straight section 112a. A first curved section 112c of the shaft 112 extends from a distal end of the second straight section 112b and curves the shaft 112 back toward the axis 111. A third straight section 112d of the shaft 112 extends from a distal end of the first curved section 112c. The first curved section 112c and the third straight section 112d are substantially coplanar with each other in a second plane. As in the case of the embodiment of FIGS. 9A-9C and as shown in FIG. 10B at 115, the first plane of the first 112a and second 112b straight sections and the second plane of the curved section 104c are angled relative to each other and are not the same plane. However, rather than the variable radius curve of the curved section 104c, as depicted in FIG. 9C, the curved section 112c defines a substantially constant radius curve.

FIGS. 11A-11D depict a delivery device 120 configured as a variation of the illustrative delivery device 110 of FIGS. 10A-10C. More particularly, the shaft sections 122a-122d are arranged such that the angle 121 between the plane of the first 122a and second 122b straight sections and the plane of the curved section 122c are substantially orthogonal to each other. Variations on the orientation of the (1)ast plane and the second plane, (2) the angle between the shaft straight sections, and/or (3) the angle between the curved shaft section and the adjacent shaft straight section, other than is shown here with respect to the devices in FIGS. 10-16, are contemplated as desired to optimize the movement that is used during a particular procedure. A handle associated with the device may extend over a portion of or the entirety of shaft section 122a and section 122b. Preferably, curved section 122c is the only portion of the shaft that penetrates into a patient's body.

Figure 12A:
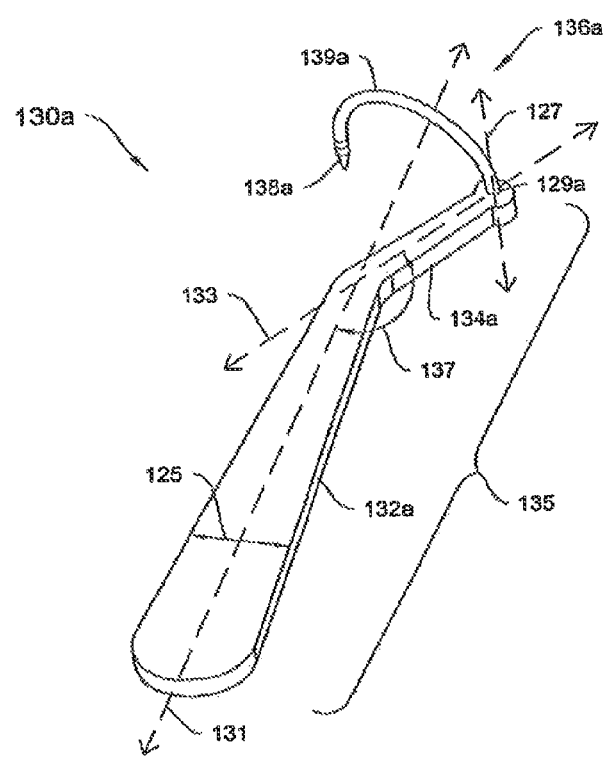
FIGS. 12A and 12B depict a pair of delivery devices having an angled handle located in a first plane and a shaft having a curved section located in a second plane.
Figure 12B:
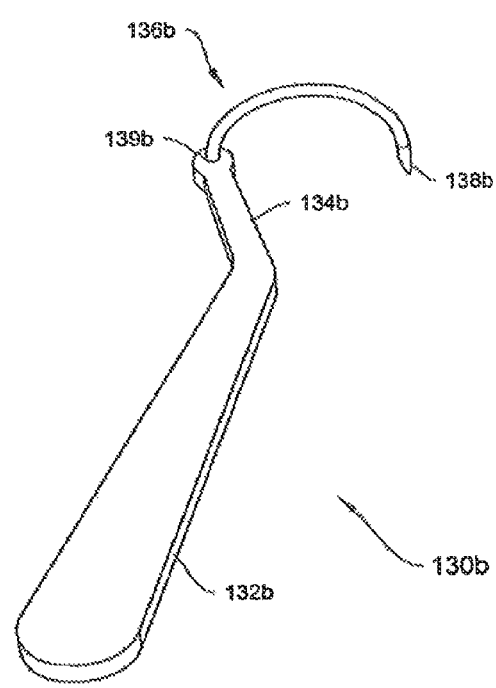

FIGS. 12A and 12B depict a pair of delivery devices 130a and 130b, each having an angled handle, according to another illustrative embodiment of the invention. The devices 130a and 130b are substantially mirror images of each other for ease of use on either side of a patients body. Accordingly, for illustrative purposes, only FIG. 12A is discussed. The handle 135 of the delivery device 130a includes a first section 132a extending along a first longitudinal axis 131 substantially in a first plane. A second section 134a of the handle 135 extends distally from, but at an angle 137 to, the axis 131 of the first section 132a. The first 132a and second 134a sections of the handle 135 are substantially coplanar in the first plane. A shaft 136a includes a curved section 139a that extends from a mounting location 129a at a distal end of the second handle section 134a. The curved section 139a first extends out of the first plane of the first 132a and second 134a handle sections, then extends back toward the first plane. In some configurations, the distal tip 138a (conically shaped in the illustrative embodiment) of the delivery device 130a extends back through the first plane. In other configurations, the distal tip 138a extends up to or short of the first plane. According to one feature, the shaft 136a rotates about an axis 127 that is substantially orthogonal to the first plane. However, according to other illustrative embodiments, the axis 127 need not be substantially orthogonal to the first plane. According to alternative illustrative embodiment, at least one of the first 132a and second 134a sections of the handle 135 tapers to have a narrower width 125 as the handle 135 extends distally toward the shaft.

Figure 13A:
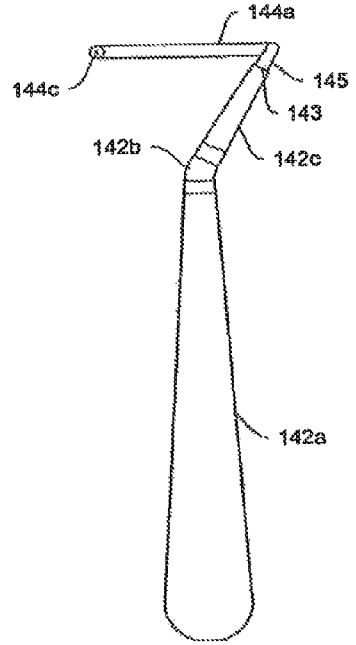
FIGS. 13A-13C depict various views of a delivery device having a handle with first and second substantially straight sections located substantially in a first plane and angled relative to each other, a shaft having a curved section located substantially in a second plane, and a transitional section extending between a distal end of the handle and a proximal end of the curved section of the shaft according to an illustrative embodiment of the invention.
Figure 13B:
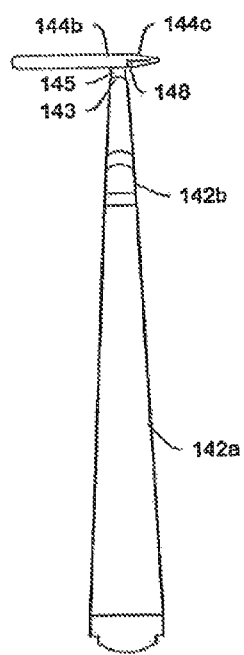
Figure 13C:
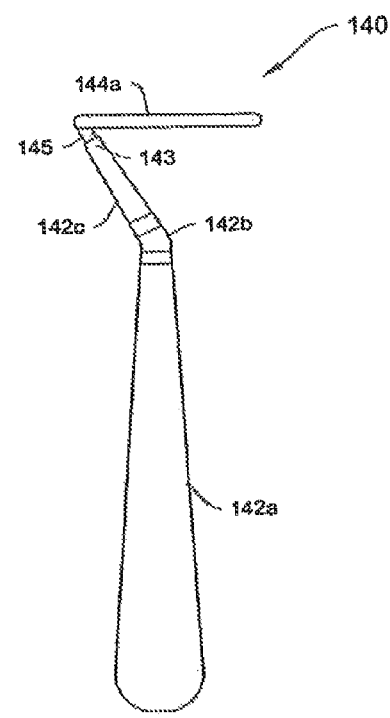

FIGS. 13A-13C depict various views of a delivery device having a handle 142 with first 142a and second 142c substantially straight sections located substantially in a first plane and angled relative to each other at 142b, a transitional portion 145 extending out of a distal end 143 of the handle 142, and a shaft 144 extending from a distal end of the transitional portion 145. The shaft includes curved section 144a, a straight section 144b, and terminates in a conical tip 144c.

The transitional portion 145 interfits and extends axially out of the distal end 143 of the second handle section 142c to affix the shaft 144 to the handle 142. As a result, the transitional portion 145 is substantially co-planar with the handle 142 in the first plane. The curved section 144a of the shaft 144 is shaped substantially like the curved section 122c of FIG. 11 and extends from a distal end of the transitional portion 145. The straight section 144b of the shaft 144 extends from a distal end of the curved section 144a. The curved section 144a and the straight section 144b are substantially coplanar in a second plane. According to the illustrative embodiment of FIGS. 13A-13C, the first and second planes are substantially orthogonal to each other. However, the first and second planes may be at any suitable angle (e.g., about 10, 20, 30, 45, 60, 70 or 80 degrees) to each other. In another illustrative embodiment of FIGS. 13A-13C, the first and second sections 142a and 142c of the handle 142 are at an angle of about 150 degrees to each other. However, first and second sections 142a and 142c of the handle 142 may be at any suitable angle (e.g., about 80, 90, 100, 110, 120, 130, 140, 160, 170 or 180 degrees) to each other.

To provide structural reinforcement, sections 142b and 142c have a cross sectional diameter that tapers to be smaller at the distal end 143 of the handle 142. Additionally, rather than having the tapered section 17c of the transitional portion 17 being formed as part of the shaft 14, as shown in FIG. 1, the tapered portions 142a, 142b, and 142c of the embodiment of FIG. 13 are formed as part of the handle 142. According to one feature, this configuration reduces the length of the transitional portion 145 and thus, provides improved structural support for the curved section 144a. Preferably, in operation, neither the handle 142 nor the transitional portion 145 extends into the body of the patient, and the angle at transitional portion 145 provides a positive stop against this occurring.

Figure 14:
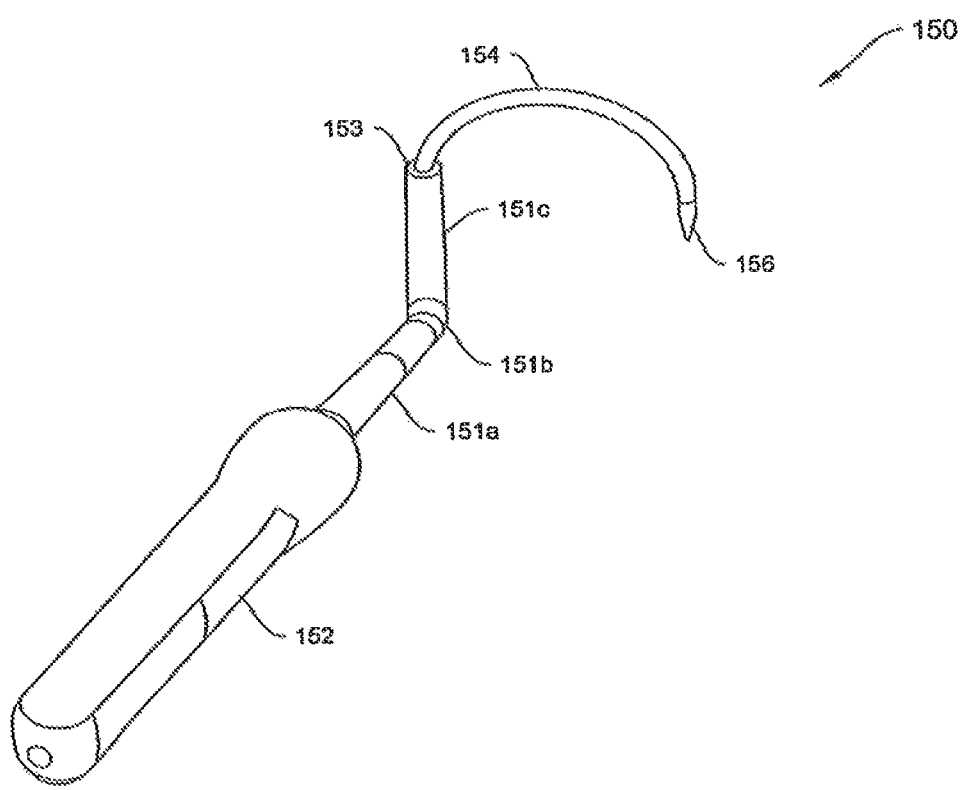
FIG. 14 depicts a variation of the illustrative embodiment of FIGS. 13A-13C, wherein the handle includes an alternative extended structurally reinforced portion in replacement for the second straight handle section and the transitional section of the embodiment of FIGS. 13A-13C.

FIG. 14 depicts a variation of the illustrative embodiment of FIGS. 13A-13C, wherein the transitional portion 151 of the delivery device 150 includes alternative structural reinforcement sections 151a-151c. The transitional portion 151 functions in similar fashion to the handle sections 142b and 142c of FIG. 13 to provide improved structural support to the shaft 154. As shown, the shaft 154 interfits with and extends axially out of the distal end 153 of the second straight section 151c of the transitional section 151. The second straight section 151c interfits directly with the curved section of the shaft 154.

Figure 15:
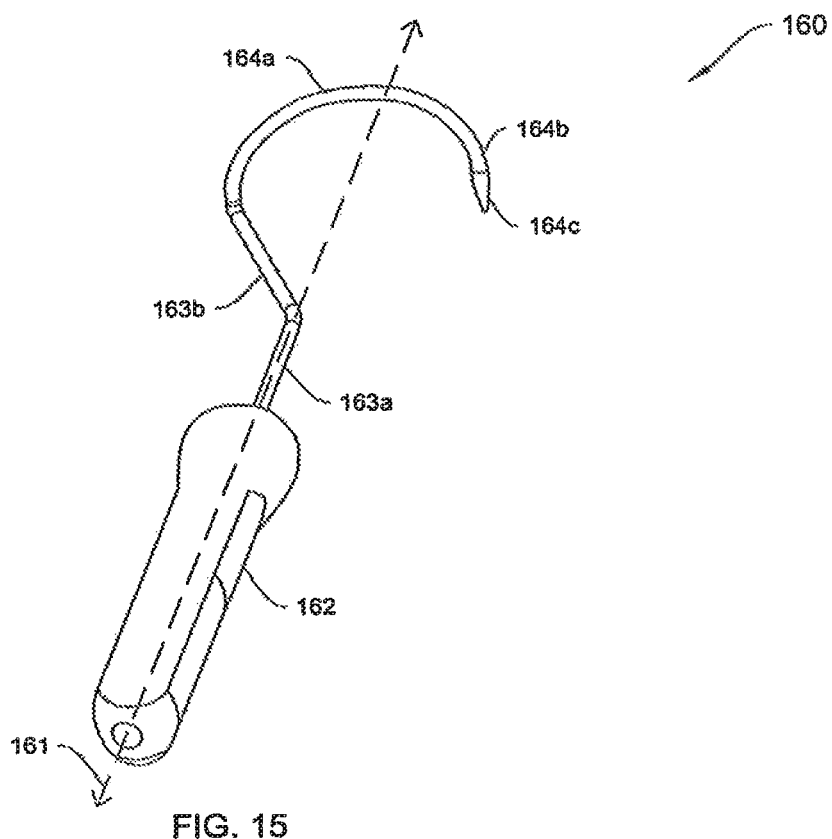
FIG. 15 depicts another variation of the illustrative embodiment of FIG. 14, wherein the first and second structurally reinforcing handle sections are replaced with unreinforced first and second substantially straight shaft sections.
Figure 16A:
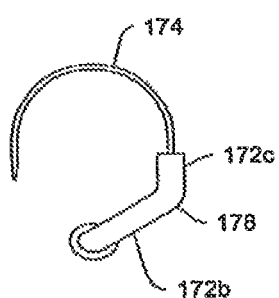
FIGS. 16A-16D depict another variation of the illustrative embodiment of FIGS. 13A-13C, wherein the handle includes first, second, and third extended structurally reinforcing handle sections in replacement for the structurally reinforcing handle sections of FIG. 14.
Figure 16C:
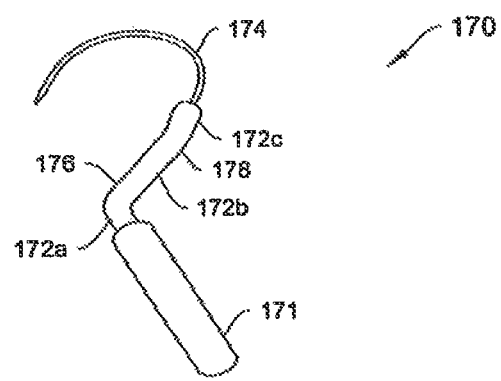
Figure 16B:
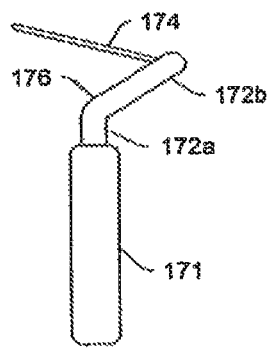
Figure 16D:
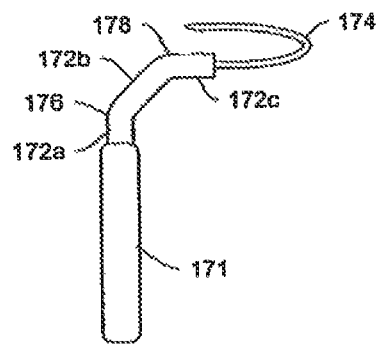

FIG. 15 depicts another variation of the illustrative embodiment of FIG. 14, wherein a shaft 164, such as the shaft 112 depicted in FIGS. 10A-10C is affixed to a distal end of a handle 162. In this embodiment, the handle does not include any distally extending supporting structures, and the shaft 164 has a substantially constant cross sectional diameter. As shown, the delivery device includes a transitional portion 163 having first straight section 163a extending distally from a distal end of the handle 162 and along a longitudinal axis 161 of the handle 162. A second straight section 163b of the transitional portion 163 extends distally from, but at an angle to the first straight section 163a. In the illustrative embodiment, the second straight section 163b is substantially coplanar in a first plane with the first straight section 163a. A curved section 164a of the shaft 164 extends from a distal end of the second straight section 163b and curves the shaft 164 back toward the axis 161. A straight section 164b of the shaft 164 extends from a distal end of the curved section 164a. The curved section 164a and the straight section 164b are substantially coplanar with each other in a second plane. As in the case of the embodiment of FIGS. 11A-11D and as shown in FIG. 15, the first plane of the first 163a and second 163b straight sections and the second plane of the curved section 164a are angled relative to each other and are not the same plane.

FIGS. 16A-16D depict various views of another illustrative delivery device 170, which illustrates another variation of the illustrative embodiment of FIGS. 13A-13C. In this variation, the sections of the transitional portion includes two elbow bends 176 and 178 as opposed to the single bend depicted in the prior embodiments. With this configuration, and depending on the elbow bends employed, the handle 171 and the transitional sections 172a-172c may be coplanar, with only the shaft 174 being in a different plane. Alternatively, the transitional portion 172 may be configured such that one or more of the transitional sections 172a-172c are substantially in a third plane different from the plane of the handle 171 and/or the shaft 174.

Figure 17:
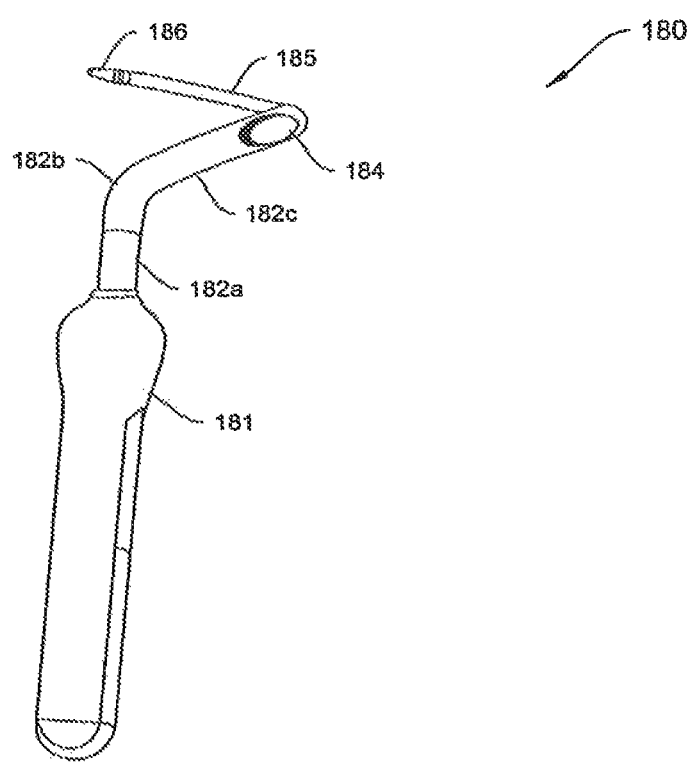
FIG. 17 depicts a delivery device including a button-like protrusion on an extended structurally reinforcing section of the handle to provide a finger hold for a medical operator according to an illustrative embodiment of the invention.

FIG. 17 depicts another illustrative delivery device 180 configured similarly to the delivery devices of FIGS. 13A-13C. According to another feature of the invention, the delivery device 180 includes a button like finger support 184 located on a reinforced section 182c of the transitional portion 182 for improving a medical operator's grasp of the device 180. As in previously discussed embodiments, one or more of the transitional sections 182a-182c may be formed as shaft sections or handle sections and the button like feature may be located on a section of the shaft or handle. The shaft includes a curved section 185 and terminates in a conical tip 186.

Figure 18:
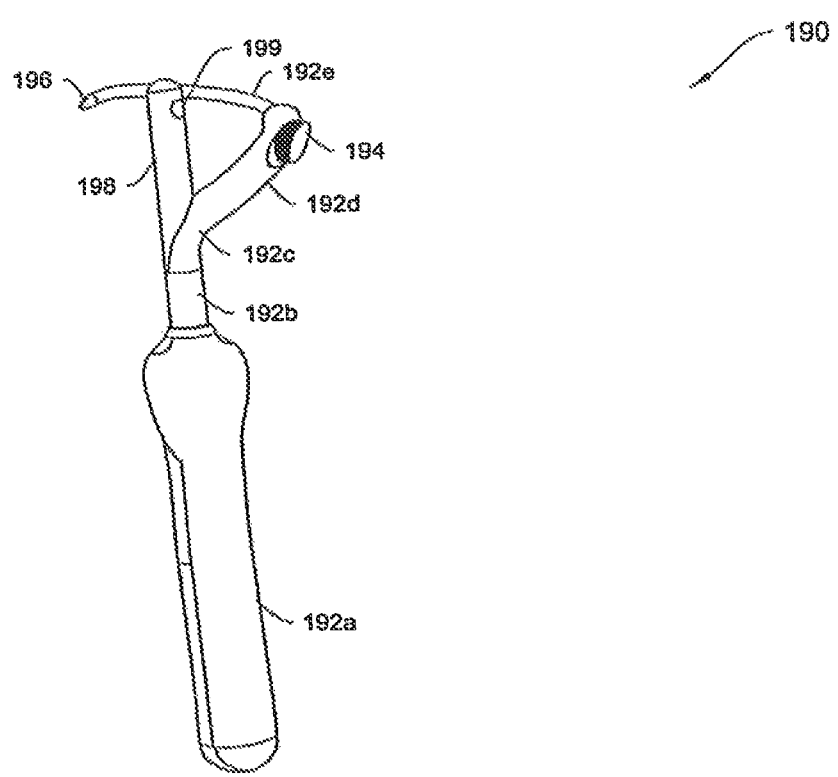
FIG. 18 depicts a variation of the delivery device of FIG. 17 including an alignment post according to another illustrative embodiment of the invention.
Figure 19:
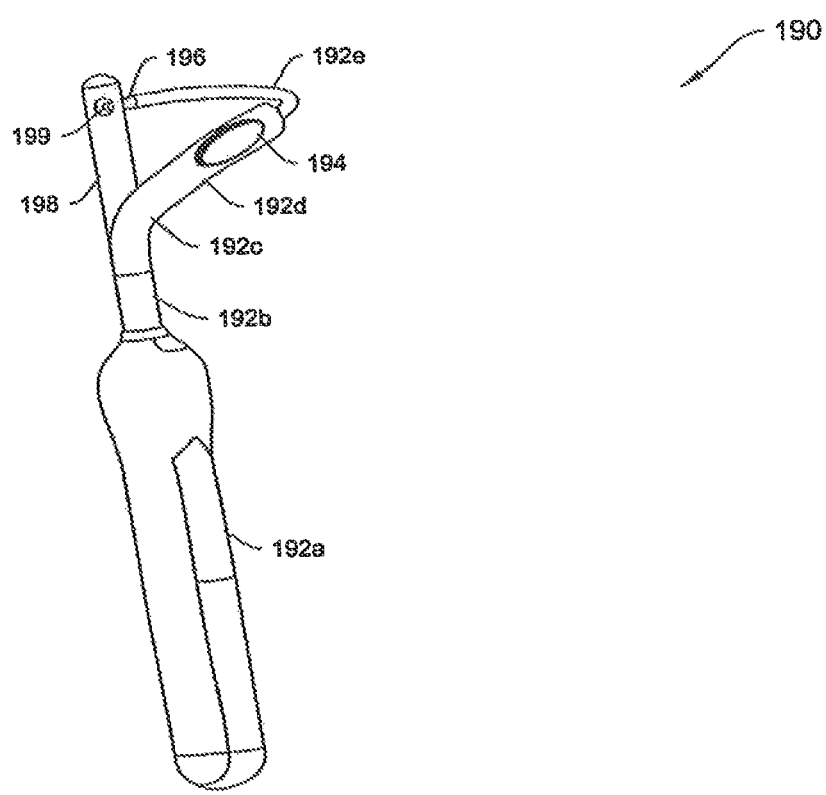
FIG. 19 depicts an alternative view of the delivery device of FIG. 18 illustrating an alignment hole in the alignment post for positioning a distal end of the shaft relative to a patient according to an illustrative embodiment of the invention.

FIGS. 18 and 19 depict another variation on the delivery device 180 of FIG. 17. In this illustrative embodiment, the delivery device 190 further includes a distally extending center post 198. To improve visibility, the center post 198 includes a sighting aperture 199, through which a medical operator can view the position of the shaft 192 generally and the conical tip 196 specifically. The post 198 also helps in orientating and guiding the conical tip 196 through the obturator foramen. The post 198 may also be used as a rotational and resting point to stabilize the shaft 192 during tissue penetration. The post 198 may also prevent the operator from inadvertently penetrating too deep and damaging organs and vessels. To open the gap or distance between the conical tip 196 and the alignment post 198, the axial extension of the alignment post 198 may be adjusted.

Any of the delivery devices described above may be used to deliver and place any suitable implant, such as a sling (e.g., a knitted mesh), or a sling assembly, at an anatomical site in a patient's body. Additionally, any suitable mechanism may be employed to associate the sling assembly with the shaft of the delivery device. In a preferred embodiment, the sling assembly does not affix, attach, connect or join with the shaft of the delivery device(s). Instead it hooks onto the delivery device, preferably in a loose and removable fashion.

Without limitation, exemplary sling assembly configurations that may be operable with illustrative embodiments of the invention may be found in the patents and patent applications cited herein, and U.S. patent application Ser. No. 10/641,170; U.S. patent application Ser. No. 10/641,192; U.S. provisional Patent Application Ser. No. 60/495,439, U.S. patent application Ser. No. 10/640,838; U.S. provisional Patent Application Ser. No. 60/403,555; U.S. provisional Patent Application Ser. No. 60/465,722; U.S. patent application Ser. No. 10/460,112; and U.S. patent application Ser. No. 09/096,983, the entire contents of all of which are incorporated herein by reference.

In one exemplary sling assembly, the length of the sling is shorter than the length of the sleeve, and the sling does not connect to the sleeve or anything else. The sling assembly inhibits the medical operator from gripping the free ends of the sling and inadvertently tensioning the sling. This feature may be further enhanced by making the sling long enough to support the urethra but not long enough to expose the ends of the sling outside the body. This may have the advantage of preventing infection caused by the exposure of the sling external to the body. By way of example, an illustrative sleeve may be at least about 1 cm, 2 cm, 3 cm, 4 cm, 5 cm, 6 cm, 7 cm, 8 cm, 9 cm, or 10 cm longer than the sling. According to other illustrative embodiments, the sleeve may be about 10 cm, 15 cm, 20 cm, 25 cm, or 30 cm longer than the sling. In particular, in transobturator procedures, the sling may be configured to be long enough to extend to, or through, both the obturator foramen but not long enough to extend outside of the body. In other embodiments, the sling may be configured in length to extend outside of the body, when placed, and the ends then trimmed to length by the physician to a point just under the skin.

FIGS. 20A-20D depict various views of an exemplary sling assembly of the type that may be employed in an illustrative embodiment of the invention. The sling assembly 210 (referring to FIGS. 20A and 20C) includes a sling 214, illustratively formed from a knitted mesh (referring to FIG. 20B), and a flexible sleeve 212, illustratively formed from a flexible polymer plastic (referring to FIGS. 20B and 20C). As depicted in FIG. 20A, the sling 214 is positioned within the sleeve 212. As depicted in FIGS. 20A and 20C, each end of the sleeve 212 connects to a dilator 211a or 211b. The dilators 211a and 211b act to secure the association loops 213a and 213b, to transition from the sling assembly to the association loops 213a and 213b and to expand tissue along a respective path during sling assembly placement.

The sleeve 212 may be made, for example, from one or more absorbent materials, such as a sponge-like material, that can optionally be pre-soaked in a drug solution, for example, in an anesthetic, anti-inflammatory, coagulating, anticoagulating, or antibiotic solution. In another embodiment, the sleeve 212 may be made from a non-wettable material, such as polypropylene, polyethylene, polyester, polytetrafluoroethylene (available from DuPont Corporation, Wilmington, Del., under the trademark TEFLON®, TYVEK®, MYLAR®, or co-polymers thereof. The non-wettable materials can also be pretreated with a therapeutically effective drug coating. The sleeve 212 is preferably transparent so that an operator will be able to see the implantable sling 214 inside the sleeve 212.

According to the illustrative embodiment, the knitted mesh 214 is made entirely of polypropylene, is approximately 1 cm in width and 45 cm in length, and terminates at free ends. In preferred embodiments, the sling 214, including both free ends, does not connect to the sleeve 212 or anything else. This feature enables a medical operator to pull on the ends of the sleeve 212 during sling assembly placement, for example, via the dilators 211a and 211b, the association loops 213a and 213b, and/or any of the delivery devices to be used for placement, without risk of stretching, curling or otherwise deforming the sling 214.

In certain embodiments, a sling of the invention has a length of about 10 to about 15 cm (about 4-6 inches) and a width of about 1 to about 3 cm, though the length and width of the sling can be adapted to the body part of the patient that requires support. By way of example, in some embodiments the sling 214 is about 45 cm in length. The sling may be rectangular or have another suitable shape. The sling may have a uniform thickness over the entire length and/or width of the sling. Alternatively, the thickness can be suitably varied at one or more locations. The thickness of the sling material may range from about 0.02 to about 0.10 cm. In one embodiment, the sling is a strip of mesh with any of a number and/or configurations of knits, weaves, or braids, e.g., the sling 242 of FIG. 23.

The sling 214 may be fabricated from any of a number of biocompatible materials, such as nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials can include polyglycolic acid, polylactic acid, and other suitable absorbable synthetic materials. Alternatively, the material for the sling may be derived from mammalian tissue(s) or a combination of mammalian tissue(s) and synthetic material(s). The sling material may be fabricated from one or more yarns, which yarns may be made from one or more materials. The sling may incorporate or be coated with one or more agents to provide a therapeutic effect, for example, to reduce discomfort, to reduce the chance of infection and/or to promote tissue growth.

In one embodiment, the edge regions of the sling can be configured differently depending on their intended placement in the body of the patient. For example, a midsection of the sling is typically located where an anatomical site, such as a mid-urethral or bladder neck location in the periurethral tissue, needs to be supported. In one illustrative embodiment, the midsection of the sling has smooth or rounded edges, hereinafter also referred to as "non-tanged" or "de-tanged." According to a further illustrative embodiment, other sections of the sling may include tangs (e.g., sharp projections or frayed edges). The tangs are generally useful for anchoring the sling 214 and/or encouraging tissue growth into the sling. Anchoring the sling in this manner generally obviates the need for additional sutures to hold the sling in place.

The tanged and non-tanged edges of sling can be formed in a plurality of ways. For example, the sling can be cut from a woven sheet, in which case the edges would be initially tanged along the entire length of the sling. One or more nontanged sections may be formed by any process that smoothes, rounds or removes the sharp edges of the tangs. For example, the tangs may be heat-smoothed by burning or melting the tangs. In one embodiment, the nontanged section has a length of about 1 to about 5 cm, preferably about 2 to about 2.5 cm, on either or both sides of the center line of the sling. Providing one or more non-tanged sections, which may be in close proximity to a sensitive anatomical site in the patient, can enhance the comfort level of the patient and reduce the potential for the edges of the tangs to erode or irritate the urethra. Alternatively, the sling can be produced from a woven tape having the approximate finished width of the sling. The smooth sides of the tape can then be trimmed off to produce the tanged sections.

Referring to FIG. 20B, an opening 216, located at a midpoint of a top portion 212a of the sleeve 212, exposes the entire width of the sling 214. A tabbed spacer 218 is located at a midpoint of a bottom side 212b of the sleeve 212, and encloses a looped portion 219 of the bottom side 212b of the sleeve 212. The tabbed spacer 218 can be used during implantation as a visual aid to placement of the sling 214. The tabbed spacer 218 also engages the looped portion 219 of the bottom side 212b of the sleeve 212 and prohibits the sleeve 212 from sliding off, or otherwise being removed from, the sling 214 during sling assembly placement. Preferably, the tabbed spacer 218 must be cut to enable the sleeve 212 to slide off the sling 214. This feature ensures that the sleeve 212 cannot be removed simply by applying a pulling force, such as that applied to the sling assembly ends by a medical operator during sling assembly placement. After the sling assembly is positioned within the patient, a cut is made through the center of the tabbed spacer 218, and thus through the looped portion 219 of the bottom side 212b of the sleeve 212. The sleeve 212 is then slid off of the sling 214, out of the body of the patient, and discarded, along with the dilators 211a and 211b.

Figure 21:
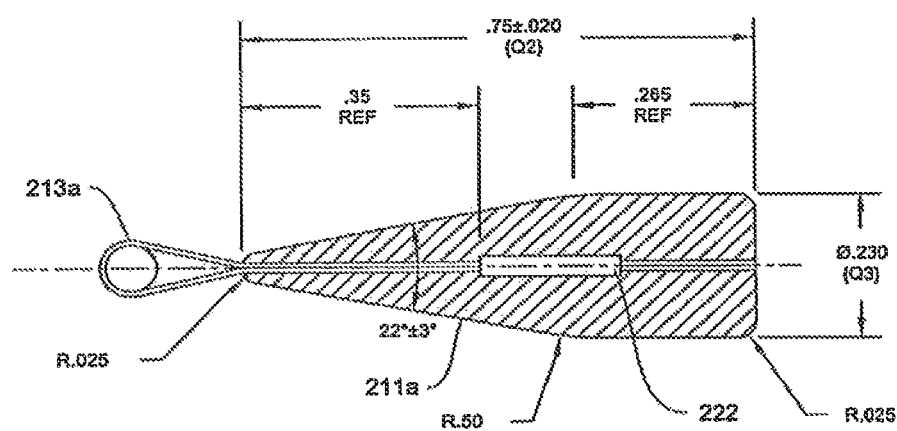
FIG. 21 is a longitudinal cross sectional view of a dilator and an association loop according to an illustrative embodiment of the invention.

FIG. 21 is a longitudinal cross sectional view of a dilator and an association loop according to an illustrative embodiment of the invention. As depicted, the dilator 211a is preferably a rigid polymer tube of approximately 2 cm in length terminating in a conical tip. Embedded and secured along the length of the dilator 211a are two ends of a wire 222 formed from twisted metal strands. The wire 222 extends from the conical tip of the dilator 211a to form an association loop 213a. The association loop 213a extending from each conical tip is preferably approximately 15 mm in length. The association loop 213a is preferably deformable, but generally shape-retaining. Preferably, the dilator 211b and the association loop 213b, as depicted in FIGS. 20A-20C, have substantially the same configurations as the dilator 211a and the association loop 213a, respectively.

Figure 22:
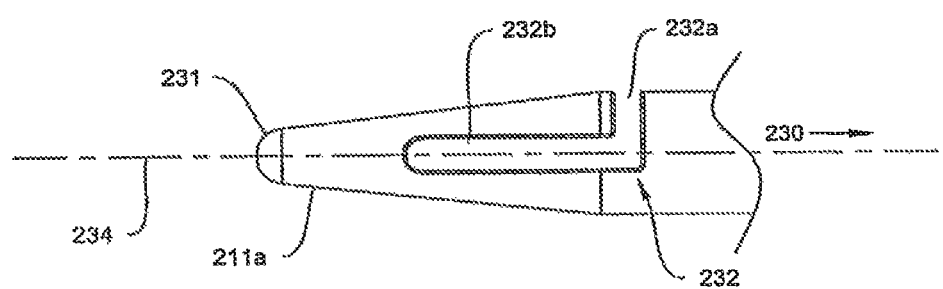
FIG. 22 is a side view of an L-slot in a distal end of a shaft of a delivery device according to an illustrative embodiment of the invention.

FIG. 22 is a side view of an L-slot in a distal end of a shaft of a delivery device according to an illustrative embodiment of the invention. For example, an L-slot 232 is preferably positioned on the distal end 19 of the shaft 14 as depicted in FIG. 1. Referring to FIG. 22, the L-slot 232 is preferably formed from a first channel 232a approximately 2 mm in length and 1 mm in width extending radially into the shaft 230 and a second channel 232b approximately 5 mm in length and 1 mm in width extending distally along the length of the distal end 231 of the shaft 230 from an inner terminal end of the first channel 232a. As discussed in more detail below, in certain illustrative embodiments, the first association loop 213a slides radially into the first channel 232a and along the second channel 232b to hook one end of the sling assembly onto the distal end 231 of the shaft 230 of a delivery device. This process may be repeated with the second association loop 213b and the same (after unhooking the first association loop 213a off the delivery device) or a second delivery device.

An advantage of the L-slot 232 configuration is that the association loops 213a and 213b remain free to slide along the respective second channels 232b. When slid to a proximal most position in the respective second channels 232b, the association loops 213a and 213b may be slid radially out of the respective first channels 232a to unhook the sling assembly from the delivery device(s) with a minimum of effort. Alternatively, during withdrawal of the delivery device(s), the distally extending orientation of the respective second channels 232b causes the association loops 213a and 213b to slide to the distal most positions in the respective L-slots 232. This tends to maintain the association loops 213a and 213b, and thus the sling assembly, hooked onto the respective second channels 232b during withdrawal of the delivery device(s).

In some alternative configurations, the second channel of an L-slot extends proximally, rather than distally, along the distal end of a shaft of any delivery device of the invention. An L-slot may be preferably formed from a first channel approximately 2 mm in length and 1 mm in width extending radially into the shaft, and a second channel approximately 5 mm in length and 1 mm in width extending proximally along the length of the distal end from an inner terminal end of the first channel. When pushing or inserting the shaft of the delivery device into the body of a patient, the proximally extending orientation of the second channel causes the association loops, for example the association loop 213a as depicted in FIG. 21, to slide to a proximal most position in the L-slot. This tends to maintain the association loop, and thus the sling assembly comprising the association loop, hooked onto the second channel during insertion of the shaft of the delivery device into the body.

In some configurations, the first channel of the L-slot extends into the shaft from radially inner location along the surface of the shaft. However, in other embodiments, the first channel of the L-slot extends into the shaft from a radially outer surface of the shaft. Additionally, the arrangement by which the sling assembly is associated with the shaft end can take numerous other forms as known in the art.

Figure 23:
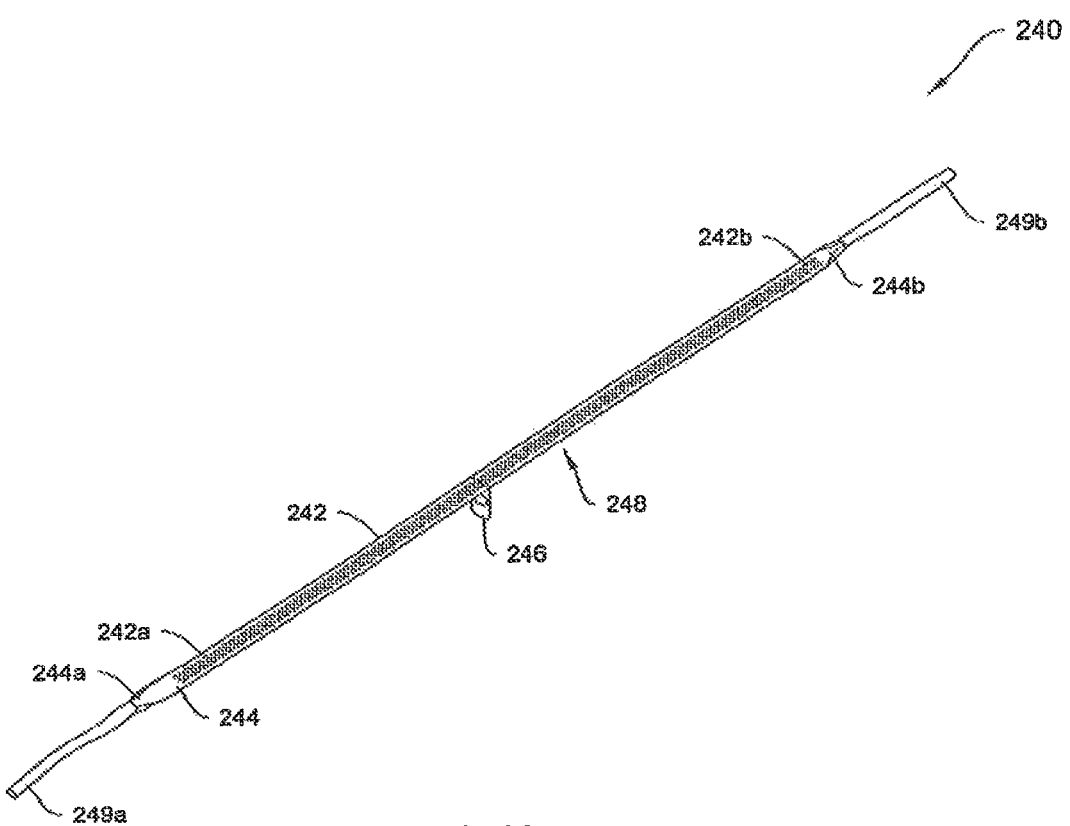
FIG. 23 depicts a sling assembly including guide tubes according to another illustrative embodiment of the invention.

FIG. 23 depicts a sling assembly 240 according to an alternative embodiment of the invention. The sling assembly 240 includes the guide tubes 249a and 249b at respective ends of the sleeve 244. The guide tubes 249a and/or 249b may taper in a direction toward or away from the midpoint of the sling assembly 240 depending on into which end of the guide tube a delivery device shaft is to be inserted. The guide tubes may be affixed to the sling assembly ends by any suitable mechanism, including gluing, heat bonding, shrink tubing or the like. In certain embodiment, the guide tubes 249a and 249b are designed to slide onto the shaft of a delivery device of the invention, and preferably the inner diameter of the guide tube is larger than the diameter(s) of the curved shaft or the diameter(s) of at least one section of the shaft, e.g., the distal end of the shaft.

Figure 24A:
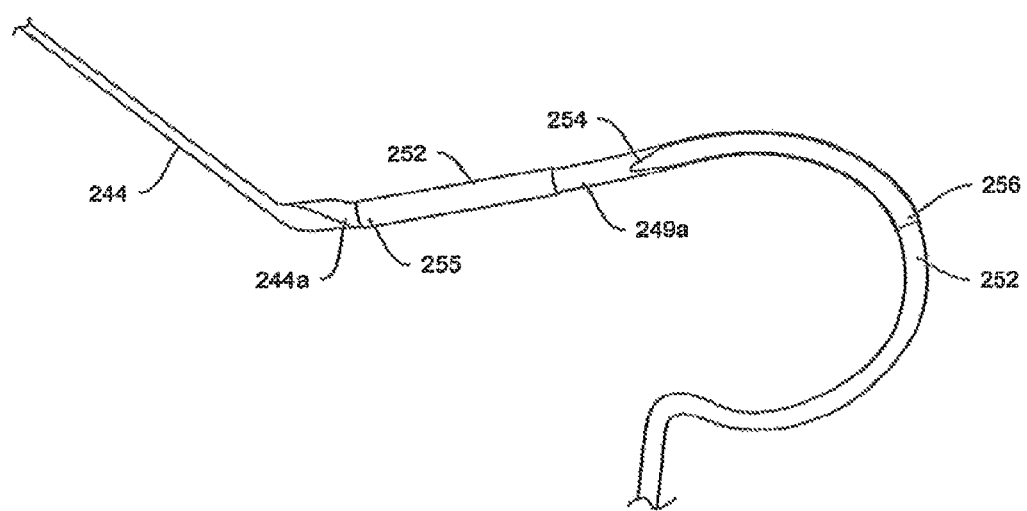
FIGS. 24A and 24B depict a shaft of a delivery device inserted into a guide tube according to two different illustrative embodiments.
Figure 24B:
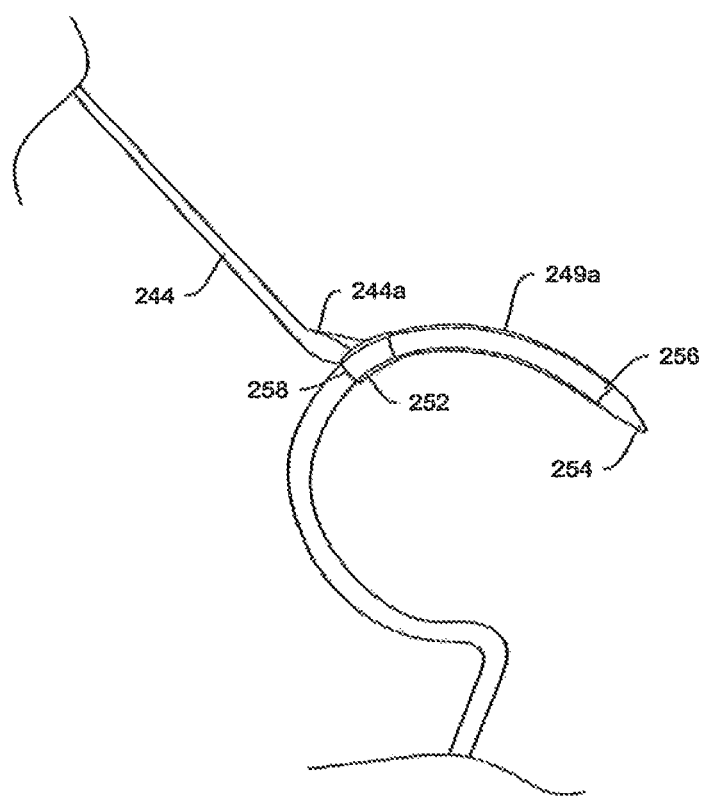
Figure 25A:
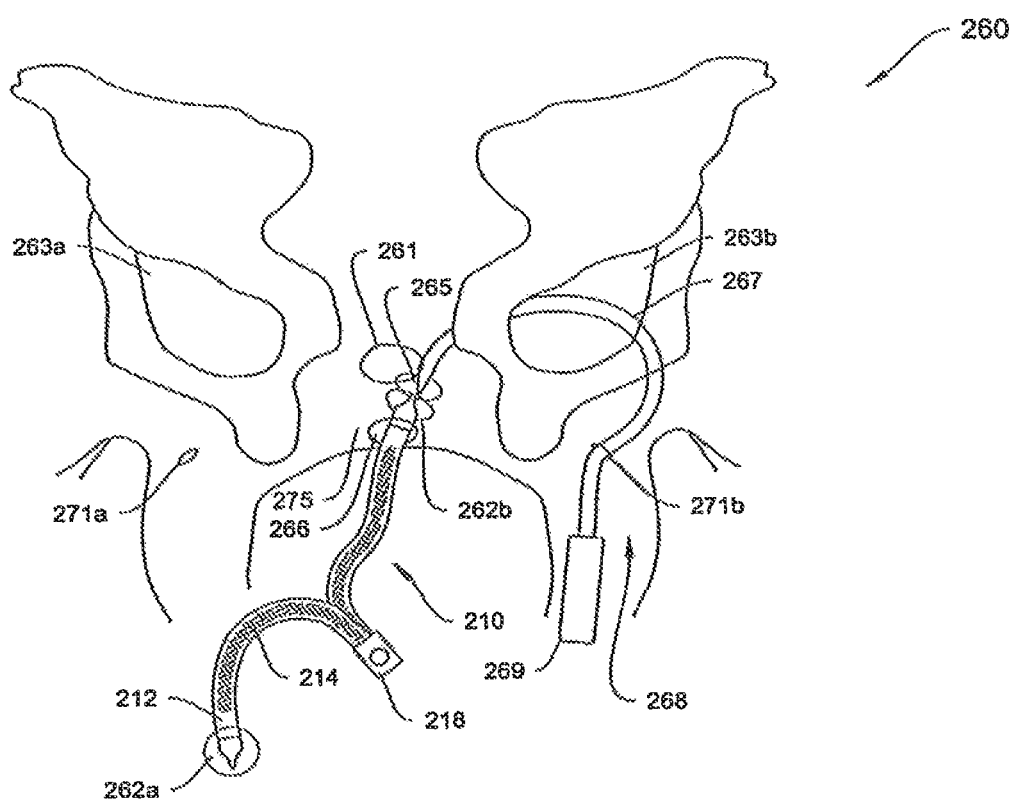
FIGS. 25A-25C depict two illustrative trans-obturator approaches.
Figure 25B:
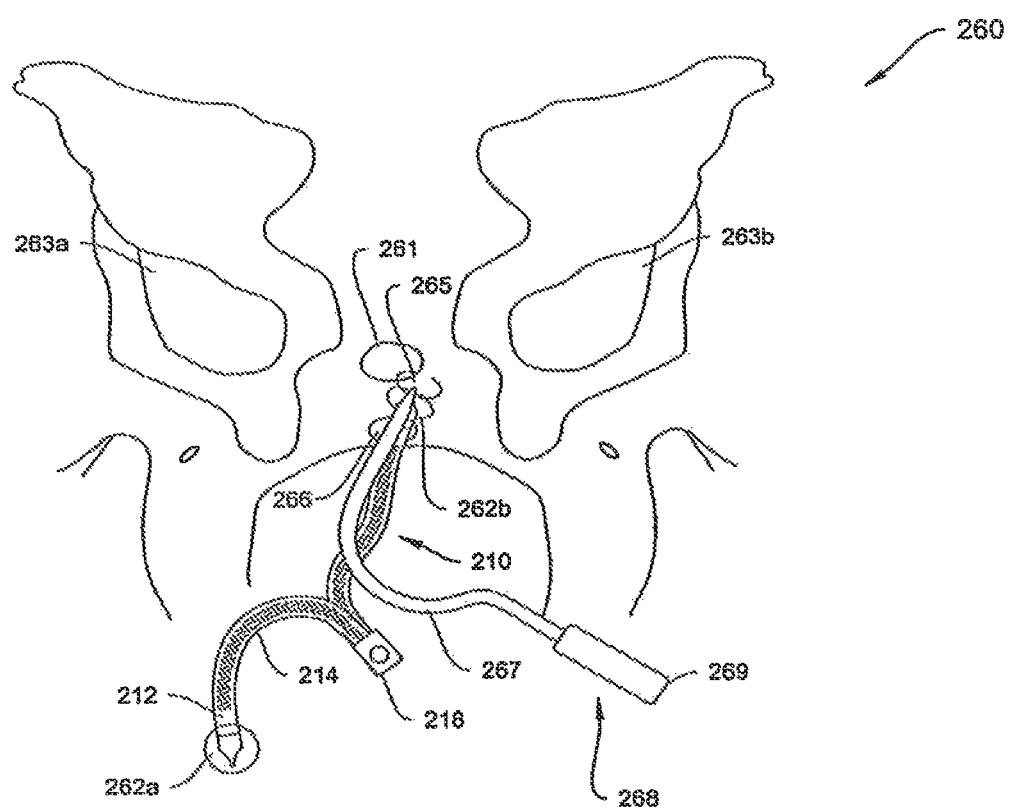

FIGS. 24A and 24B depict two illustrative examples of how the guide tubes 249a and 249b may be slid onto the shaft 252 of a delivery device. As depicted in FIG. 25A, according to one approach, the conical tip 254 is inserted into the end 256 of the guide tube 249a not bonded to the sleeve 244a of the sling assembly 244. As depicted in FIG. 25B, in an alternative embodiment, the conical tip 254 of the shaft 252 is inserted into the guide tube end 255 that is bonded to the sleeve 244a of the sling assembly 244. Preferably, the guide tube 249a slides easily on and off the shaft 252 of the delivery device. However, in alternative embodiments, the sling assembly ends may include receptacle connectors or mating structures, for forming a secure attachment between the sling assembly end and the distal end of the delivery device shaft.

Figure 25C:
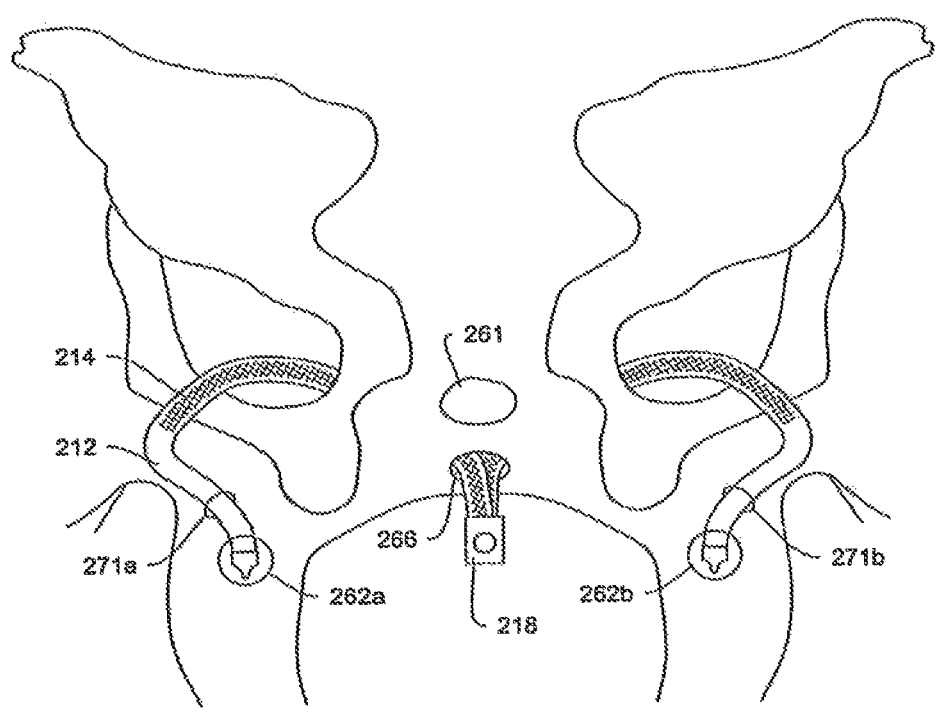

Described now with respect to FIGS. 25A-25C are various illustrative methods for delivering an implant, such as a sling or sling assembly, to an anatomical site in the body of a patient. The illustrative methods include trans-obturator approaches. Other approaches, such as for example suprapubic, prepubic, and transvaginal approaches are disclosed in the patents and patent applications cited herein. All operative combinations between the disclosed delivery devices and these alternative procedures are contemplated. Any of the delivery devices described above may be employed to create a passage through body tissue, for example, from the inferior pubic ramus through the obturator foramen to the vagina or the reverse according to the methodologies described herein.

According to one exemplary methodology, referring to FIG. 25A, a first incision 271b is made on the inside of the patient's thigh, for example, about 1 cm outside the external margin of the labia majora. The medical operator inserts the shaft 267 of the delivery device 268, tip first, into the first incision 271b and continues to penetrate a first obturator foramen 263b. With a rotating wrist motion, the shaft 267 is guided along the posterior ischiopubic ramus to a vaginal incision 266 on the vaginal wall 275. After a distal portion 265 of the shaft 267 emerges out of the vaginal wall 275, the operator associates a distal end of the shaft 267 with a first end of a sling assembly 210.

According to one illustrative embodiment, the distal end of the shaft 267 includes an L-slot onto which an association loop located at the first end of the sling assembly may be hooked. More particularly, and also with reference to FIGS. 20A-22, a first association loop, such as the association loop 213a is slid over the distal end 265 of the shaft 267 of the delivery device and radially into a first channel, such as the channel 232a of an L-slot, such as the L-slot 232. The association loop 213a is then moved distally away from the delivery device within a second channel, such as the channel 232b, to hook one end of the sling assembly onto the delivery device. The delivery device is then withdrawn from the ishiopubic incision, drawing the end of the sling assembly through the passage created by the shaft 267. The orientation of the L-slot 232 with respect to the ishiopubic approach ensures that the association loop 213a is tensioned toward the closed, distal end of the L-slot 232 as the delivery device is withdrawn. Subsequent to withdrawal, the association loop 213a and the distal end 265 of the shaft 267 are oriented perpendicularly to each other, and then the association loop 213a is unhooked from the delivery device.

The process can then be repeated with the same or a second delivery device on the contralateral side of the body with a second association loop, such as the association loop 213b of the sling assembly 210. Optionally, a single cystoscopy may be performed with two delivery devices in place, prior to withdrawal of the delivery devices to verify integrity of the bladder. Cystoscopy could also be performed, as desired, after each placement of a delivery device on a side of the body.

Referring also to FIG. 24A, in an alternative approach, a guide, such as the guide tubes 249a or 249b, extends from each sling assembly end 262a and 262b. The guide tube can be slid over the distal end 265 of the shaft 267 according to the approach of FIG. 24A. Then, the operator withdraws the shaft 267 of the delivery device back out of the obturator foramen 263b, bringing the sleeve end 244a or 244b of the sling assembly 240 out of the first thigh incision 271b.

Once again, the process can then be repeated with the same or a second delivery device on the contralateral side of the body with a second association guide tube. Optionally, a single cystoscopy may be performed with two delivery devices in place, prior to withdrawal of the delivery devices to verify integrity of the bladder. Cystoscopy may also be performed, as desired, after each placement of a delivery device on a side of the body. FIG. 25C provides a conceptual drawing showing the sling assembly positioned prior to cutting the tabbed divider 218. Once desired placement of the sling assembly is achieved, the tabbed spacer 218, and thus the looped portion 219 of the bottom side 212b of the plastic sleeve 212, is cut. Then, by pulling on the dilators or guide tubes, as the case may be, the medical operator can slide the sleeve 212 off the sling 214 and remove it from the body. The delivery device(s) and the plastic sleeve 212, including the dilators or the guide tubes, as the case may be, may then be discarded. In some embodiments the sling ends are anchored or otherwise affixed to muscle, tissue, or bone within the pelvic region of the body. However, in preferred embodiments, the sling ends remain unanchored.

Referring to FIG. 25B, in an alternative embodiment, the operator can reverse the direction in the trans-obturator approach by starting from a vaginal incision 266 and tunneling through the obturator foramen 263a or 263b to the respective thigh incision 271a or 271b using any of the delivery devices and sling assemblies described above.

According to one illustrative embodiment, the distal end of the shaft 267 includes an L-slot onto which an association loop located at the first end of the sling assembly may be hooked. According to embodiment, the L-slot orientation is such that the second channel of the L-slot extends proximally along the shaft, as opposed to distally. With reference to FIGS. 20A-22, prior to inserting the shaft into the vaginal incisions, a first association loop, such as the association loop 213a is slid over the distal end 265 of the shaft 267 of the delivery device and radially into a first channel, such as the channel 232a of an L-slot, such as the L-slot 232. The association loop 213a is then moved proximally toward the delivery device within a second channel, such as proximally extending variation of the distally extending channel 232b, to hook one end of the sling assembly onto the delivery device. The delivery device is then inserted through the vaginal incision and out the ishiopubic incision, as described above. The orientation of the L-slot 232 with respect to the vaginal approach ensures that the association loop 213a is tensioned toward the closed, proximal end of the L-slot 232 as the delivery device is inserted into the vaginal incision and out the ishiopubic incision. After the distal tip of the delivery device exits the ishiopubic incision, the association loop 213a and the distal end 265 of the shaft 267 are oriented perpendicularly to each other, and then the association loop 213a is unhooked from the delivery device. The delivery device can then be withdrawn.

The process can then be repeated with the same or a second delivery device on the contralateral side of the body with a second association loop, such as the association loop 213b of the sling assembly 210 in FIG. 20A. Optionally, a single cystoscopy may be performed with two delivery devices in place, prior to withdrawal of the delivery devices to verify integrity of the bladder. Cystoscopy could also be performed, as desired, after each placement of a delivery device on a side of the body. Alternatively, cystoscopy could be performed after withdrawal of the delivery devices.

Referring also to FIG. 24B, in an alternative approach, a guide, such as the guide tubes 249a or 249b, depicted in FIG. 23, extends from each sling assembly end 242a and 242b. The guide tube can be slid over the distal end 265 of the shaft 267 according to the approach of FIG. 25B. Then, the operator inserts the shaft 267 of the delivery device into the vaginal incision as described above with respect to FIG. 25B. According to this embodiment, once the distal end 265 of the shaft 267 exits the ishiopubic incision, a medical operator can grasp the guide tube and withdraw the delivery device. It should be noted that the guide tubes of this embodiment are particularly sized to enable the distal tip 265 of the shaft 267 to extend out and be exposed, when inserted.

As in the above described methodologies, the process can then be repeated with the same or a second delivery device on the contralateral side of the body with a second association guide tube, such as the guide tube 249b as depicted in FIG. 23. Optionally, a single cystoscopy may be performed with two delivery devices in place, prior to withdrawal of the delivery devices to verify integrity of the bladder. Cystoscopy could also be performed, as desired, after each placement of a delivery device on a side of the body. Alternatively, cystoscopy could be performed after withdrawal of the delivery devices.

Variations, modifications, and other implementations of what is described may be employed without departing from the spirit and the scope of the invention. More specifically, any of the method, system and device features described above or incorporated by reference may be combined with any other suitable method, system or device features disclosed herein or incorporated by reference, and is within the scope of the contemplated inventions.

What is claimed is:

1. A system for treating urinary incontinence, comprising:
a flexible sleeve having a first end and a second end;
a mesh sling at least partially within the sleeve, the mesh sling being planar and defining a longitudinal axis and a transverse axis, the mesh sling being longer on the longitudinal axis than the transverse axis;
a first guide tube attached to the first end of the sleeve and a second guide tube attached to the second end of the sleeve, each of said first and second guide tubes comprising a tapering cylindrical portion, the first guide tube defining a first lumen having a longitudinal axis that is parallel with the longitudinal axis of the mesh sling, and the second guide tube defining a second lumen having a longitudinal axis that is parallel with the longitudinal axis of the mesh sling; and
a delivery device comprising:
a handle;
a shaft having a curved portion terminating in a substantially conical tip, at least the first guide tube being configured to receive the shaft at a first end of the first guide tube that is coupled with the sleeve such that a portion of the shaft is disposed with first guide tube and the conical tip extends out of a second end of the first guide tube; and
first and second straight sections, the first straight section extending along a first axis and the second straight section extending along a second axis different from the first axis.

2. The system of claim 1, wherein an inner diameter of each of the first and second guide tubes is greater than an outer diameter of the conical tip.

3. The system of claim 1, further comprising first and second receptacle connectors disposed at the first and second ends of the sling, respectively.

4. The system of claim 1, further comprising first and second mating structures disposed at the first and second ends of the sling, respectively.

5. The system of claim 1, wherein the sleeve includes a tab attached intermediate to first and second ends of the sleeve, the sleeve being removable to expose the mesh sling by cutting the tab.

6. The system of claim 1, wherein sleeve is longer than the sling.

7. The system of claim 6, wherein the sleeve is about 10 cm longer than the sling.

8. The system of claim 6, wherein the sleeve is about 20 cm longer than the sling.

9. The system of claim 6, wherein the sleeve is about 30 cm longer than the sling.

10. The system of claim 1, wherein the delivery device includes a transitional portion located intermediate to the handle and the shaft for affixing the shaft to the handle.

11. The system of claim 10, wherein at least part of the transitional portion is formed as part of the shaft.

12. The system of claim 10, wherein at least part of the transitional portion is formed as part of the handle.

13. A system for treating urinary incontinence, including:
a delivery device having:
a handle; and
a shaft having a first curved portion and a substantially conical tip at a distal terminus of the shaft; and
a sling assembly, including:
a mesh sling, the mesh sling being planar and defining a longitudinal axis and a transverse axis, the mesh sling being longer along the longitudinal axis than the transverse axis;
a flexible sleeve at least partially enclosing the mesh sling, the flexible sleeve including:
first and second guide tubes disposed at first and second ends of the flexible sleeve, respectively; and
a tab attached intermediate to the first and second ends of the sleeve, the sleeve being removable to expose the mesh sling by cutting the tab,
at least the first guide tube having a first end coupled with the sleeve, a second end, and a lumen extending therethrough, the lumen defining a longitudinal axis that is parallel with the longitudinal axis of the mesh sling and configured to receive at least a portion of the shaft.

14. The system of claim 13, wherein the first and second guide tubes are substantially cylindrical.

15. The system of claim 13, wherein the first and second guide tubes are tapered.

16. The system of claim 13, further comprising first and second mating structures disposed at the first and second ends of the sling, respectively.

17. The system of claim 13, wherein sleeve is longer than the sling.

18. The system of claim 17, wherein the sleeve is about 10 cm longer than the sling.

19. The system of claim 17, wherein the sleeve is about 20 cm longer than the sling.

20. The system of claim 17, wherein the sleeve is about 30 cm longer than the sling.

21. The system of claim 13, further comprising first and second receptacle connectors disposed at the first and second ends of the sling, respectively.

* * * * *